US012616546B2

(12) United States Patent
Zhou

(10) Patent No.: US 12,616,546 B2
(45) Date of Patent: May 5, 2026

(54) SURGICAL DEVICE WITH THREE POSITION SAFETY TRIGGER ASSEMBLY

(71) Applicant: Covidien LP, Mansfield, MA (US)

(72) Inventor: Xiao Zhou, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/837,087

(22) PCT Filed: Feb. 10, 2022

(86) PCT No.: PCT/CN2022/075827
§ 371 (c)(1),
(2) Date: Aug. 8, 2024

(87) PCT Pub. No.: WO2023/150964
PCT Pub. Date: Aug. 17, 2023

(65) Prior Publication Data
US 2025/0134616 A1 May 1, 2025

(51) Int. Cl.
*A61B 17/072* (2006.01)
*A61B 90/00* (2016.01)
(Continued)

(52) U.S. Cl.
CPC ........ *A61B 90/03* (2016.02); *A61B 17/07207* (2013.01); *A61B 2017/00398* (2013.01); *A61B 2017/2913* (2013.01)

(58) Field of Classification Search
CPC .............. A61B 90/03; A61B 17/07207; A61B 2017/00398; A61B 2017/2913
(Continued)

(56) References Cited

U.S. PATENT DOCUMENTS 8,006,885 B2 * 8/2011 Marczyk .......... A61B 17/07207
227/176.1
2011/0155785 A1 * 6/2011 Laurent .......... A61B 17/320016
74/109
(Continued)

FOREIGN PATENT DOCUMENTS

CA       3 072 771 A1    2/2019
CN       107809965 A     3/2018
(Continued)

OTHER PUBLICATIONS

International Written Opinion for International Application No. PCT/CN2022/075827 mailed Nov. 16, 2022 (4 pages).
(Continued)

*Primary Examiner* — Linda J. Hodge

(57) ABSTRACT

A powered surgical device (10) includes a safety trigger assembly (62) that is movable from a safe position to an intermediate position, and subsequently to a fire-ready position. The safety trigger assembly (62) prevents firing of the surgical device (10) unless the safety trigger assembly (62) is in the fire-ready position and includes at least one safety button (120, 134) that extends through an outer housing (18) of the surgical device (10) and is accessible to a clinician to move the safety trigger assembly (62) to the fire-ready position. The surgical device (10) includes the outer housing (18) that shields the at least one safety button (120, 134) when the safety trigger assembly (62) is in the safe position to prevent inadvertent movement of the safety trigger assembly (62) from the safe position to the fire-ready position.

18 Claims, 17 Drawing Sheets

(51) Int. Cl.
     *A61B 17/00*      (2006.01)
     *A61B 17/29*      (2006.01)

(58) Field of Classification Search
     USPC ....................................................... 227/175.1
     See application file for complete search history.

(56)                References Cited

U.S. PATENT DOCUMENTS

2017/0290583 A1   10/2017  Reed et al.
2017/0296176 A1*  10/2017  Contini ............. A61B 17/0686

FOREIGN PATENT DOCUMENTS

| CN | 212089645 U | 12/2020 |
|----|-------------|---------|
| CN | 113907822 A | 1/2022 |
| WO | 2020077531 A1 | 4/2020 |

OTHER PUBLICATIONS

International Search Report for International Application No. PCT/CN2022/075827 mailed Nov. 16, 2022 (6 pages).
Extended European Search Report for European Patent Application No. 22925326.5 mailed Oct. 6, 2025, 12 pages.

* cited by examiner

SURGICAL DEVICE WITH THREE POSITION SAFETY TRIGGER ASSEMBLY

CROSS-REFERENCE TO THE RELATED APPLICATIONS

This application is a National Stage Application of PCT/CN2022/075827 filed 10 Feb. 2022, which application is incorporated herein by reference. To the extent appropriate, a claim of priority is made to the above disclosed application.

FIELD

This disclosure is directed to powered surgical devices and, more particularly, to powered surgical stapling devices.

BACKGROUND

Various types of surgical devices used to endoscopically treat tissue are known in the art, and are commonly used, for example, for closure of tissue or organs in transection, resection, and anastomoses procedures, for occlusion of organs in thoracic and abdominal procedures, and for electrosurgically fusing or sealing tissue.

One example of such a surgical device is a surgical stapling device. Typically, surgical stapling devices include a tool assembly having an anvil assembly and a cartridge assembly, and a drive assembly. The drive assembly includes a flexible drive beam and a clamp member that is supported on a distal end of the drive beam. The drive assembly is movable to advance the clamp member through the tool assembly to move the tool assembly from an open position to a clamped position, and to advance an actuation sled and knife through the cartridge assembly to eject staples from the cartridge assembly and to cut tissue clamped between the anvil and cartridge assemblies.

Surgical stapling devices can be manually actuated devices or powered stapling devices. Powered stapling devices include one or more actuation buttons to activate a motor to initially advance the drive assembly and move the tool assembly from the open position to a clamped position, and subsequently advance the actuation sled and knife through the tool assembly to fire the stapling device, i.e., eject staples from the cartridge assembly and cut tissue clamped between the cartridge and anvil assemblies. Such devices include a first switch mechanism to stop the motor when the tool assembly is in the clamped position, and a second switch mechanism that must be actuated to enable activation of the motor to facilitate firing of the stapling device. The need for two separate switch mechanisms increases the cost of the stapling device. In addition, accidental actuation of the second switch mechanism may compromise the safety of the surgical stapling device.

A continuing need exists in the art for a powered stapling device that includes a safety switch mechanism that needs only a single micro-switch, and/or a safety switch mechanism that is less prone to accidental actuation.

SUMMARY

A surgical device includes a safety trigger assembly that is movable from a safe position to an intermediate position, and subsequently to a fire-ready position. The safety trigger assembly prevents firing of the surgical device unless the safety trigger assembly is in the fire-ready position and includes at least one safety button that extends through an outer housing of the surgical device and is accessible to a clinician to move the safety trigger assembly to the fire-ready position. The surgical device includes an outer housing that shields the at least one safety button when the safety trigger assembly is in the safe position to prevent inadvertent movement of the safety trigger assembly from the safe position to the fire-ready position.

Aspects of the disclosure are directed to a powered handle assembly for a surgical device that includes an outer housing, an actuation button, a rack, a motor/gear assembly, a first safety switch, a bias arm, and a safety trigger assembly. The outer housing defines a cavity and supports the actuation button. The rack includes teeth and is supported within the outer housing to move from a rack retracted position, to a rack clamp position, and subsequently to a rack advanced position. The motor/gear assembly is associated with the rack and is operable to move the rack from the rack retracted position, to the rack clamp position, and subsequently to the rack advanced position. The first safety switch is supported on the inner housing and is movable between a first state and a second state. In the second state, the actuation button is operable to supply power to the motor/gear assembly and in the first state, power is disrupted to the motor/gear assembly. The bias arm is supported adjacent the first safety switch and includes a cam member and an abutment member. The bias arm is movable between a first position in which the abutment member is engaged with the first safety switch to position the first safety switch in the second state, and a second position in which the safety switch is positioned in the first state. The safety trigger assembly includes at least one safety button that extends through a slot in the outer housing, and is movable from a safe position, through an intermediate position, to a fire-ready position to position the safety switch in the second state.

In aspects of the disclosure, the rack is configured to engage the bias arm as the rack moves from the rack retracted position to the rack clamp position to move the bias arm from the first position to the second position.

In some aspects of the disclosure, a first biasing member is positioned to urge the bias arm towards the second position.

In certain aspects of the disclosure, the rack is configured to engage the safety trigger assembly as the rack moves from the rack retracted position to the rack clamped position to move the safety trigger assembly from the safe position to the intermediate position.

In aspects of the disclosure, the outer housing includes a safety button shield that is positioned adjacent one end of the slot and is positioned partially about the at least one safety button when the safety trigger assembly is in the safe position to limit access to the at least one safety button.

In some aspects of the disclosure, the rack defines a cam surface, and the safety trigger assembly includes a cam member that moves along the cam surface of the rack as the rack moves from the rack retracted position to the rack clamp position to move the safety trigger assembly from the safe position to the intermediate position.

In certain aspects of the disclosure, a biasing member is positioned to urge the safety trigger assembly towards the safe position.

In aspects of the disclosure, a latch is positioned to engage the safety trigger assembly to retain the safety trigger assembly in the fire-ready position.

In some aspects of the disclosure, the safety trigger assembly includes a retainer member that is configured to engage the latch when the safety trigger assembly is in the fire-ready position to retain the safety trigger assembly in the fire-ready position.

In aspects of the disclosure, the safety switch is a micro-switch.

Other aspects of the disclosure are directed to a powered handle assembly for a surgical device including an outer housing, an actuation button, a rack, a motor/gear assembly, at least one safety switch, a bias arm, and a safety trigger assembly. The outer housing supports the actuation button and defines a cavity. The rack has teeth and is supported within the outer housing for movement from a rack retracted position, to a rack clamp position, and subsequently to a rack advanced position. The motor/gear assembly is associated with the rack and is operable to move the rack from the rack retracted position, through the rack clamp position, and subsequently to the rack advanced position. The at least one safety switch is supported within the outer housing and is movable between first and second states. The bias arm is supported adjacent to the at least one safety switch and includes a cam member and an abutment member. The bias arm is movable between a first position in which the abutment member is engaged with the at least one safety switch to position the at least one safety switch in the second state and a second position in which the at least one safety switch is positioned in the first state. The safety trigger assembly includes at least one safety button that extends through a slot in the outer housing. The safety trigger assembly is positioned to engage the at least one safety switch and is movable from a safe position, through an intermediate position, to a fire-ready position to position the at least one safety switch in the second state. The bias arm is positioned to engage the safety trigger assembly as the bias arm moves from the first position to the second position to move the safety trigger assembly from the safe position to the intermediate position.

In aspects of the disclosure, the outer housing includes a safety button shield that is positioned adjacent to one end of the slot and extends partially about the at least one safety button when the safety trigger assembly is in the safe position to limit access to the at least one safety button.

In some aspects of the disclosure, the rack is configured to engage the bias arm as the rack moves from the rack retracted position to the rack clamp position to move the bias arm from the first position to the second position.

In certain aspects of the disclosure, the at least one safety switch includes a first safety switch and a second safety switch, and the abutment member of the bias arm is engaged with the first safety switch.

In aspects of the disclosure, the safety trigger assembly is positioned to engage the second safety switch.

Other features of the disclosure will be appreciated from the following description.

BRIEF DESCRIPTION OF THE DRAWINGS

Various aspects of the disclosed surgical device are described herein below with reference to the drawings, wherein.

DETAILED DESCRIPTION

Figure 1:
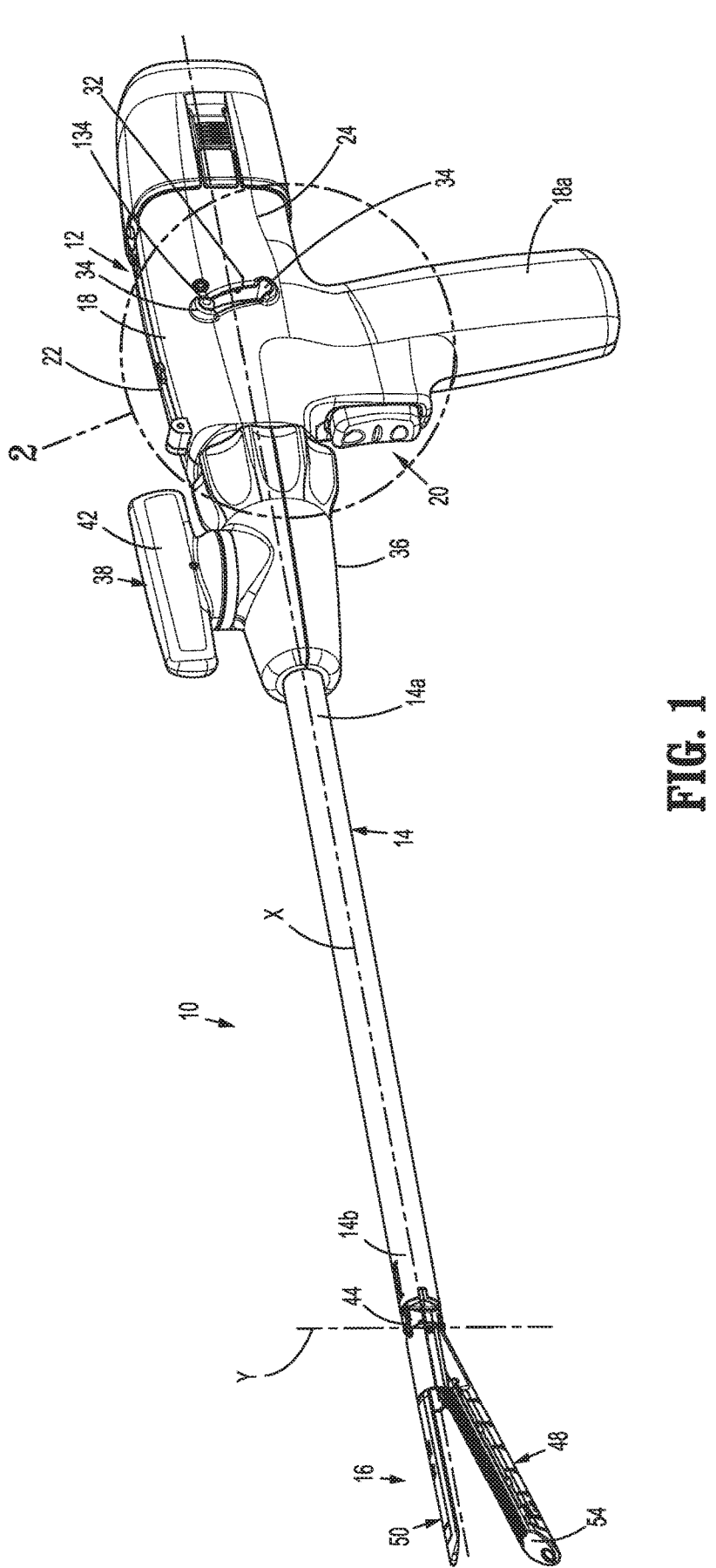
FIG. 1 is a side perspective view of a surgical device according to aspects of the disclosure in an unclamped, pre-fired position.

The disclosed surgical device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, surgeons, and support personnel.

This disclosure is directed to a powered surgical device that includes a safety trigger assembly that is movable from a safe position to an intermediate position, and subsequently to a fire-ready position. The safety trigger assembly prevents firing of the surgical device unless the safety trigger assembly is in the fire-ready position and includes at least one safety button that extends through an outer housing of the surgical device and is accessible to a clinician to move the safety trigger assembly to the fire-ready position. The surgical device includes an outer housing that shields the at least one safety button when the safety trigger assembly is in the safe position to prevent inadvertent movement of the safety trigger assembly from the safe position to the fire-ready position.

FIG. 1 illustrates a surgical device shown generally as stapling device 10 which includes a powered handle assembly 12, an elongate body or adapter assembly 14, and a tool assembly 16. The handle assembly 12 includes an outer housing 18 that forms a stationary handle portion 18a and an actuation button or buttons 20 that control operation of the various functions of the stapling device 10, e.g., clamping and firing of the stapling device 10. In aspects of the disclosure, the outer housing 18 of the handle assembly 12 is formed from outer housing half-sections 22 and 24 that are secured together to define a cavity 26 (FIG. 2) that encloses internal components of the surgical device 10. In aspects of the disclosure, the stationary handle portion 18a of the outer housing 18 supports batteries 28 and a motor/gear assembly 30. Each of the half-sections 22 and 24 of the outer housing 18 defines a curved slot 32 (only one is shown) and includes a safety button shield 34 positioned at each end of the curved slot 32.

The elongate body 14 of the stapling device 10 has a proximal portion 14a and a distal portion 14b and defines a longitudinal axis "X". The proximal portion 14a of the elongate body 14 supports a rotation knob 36 and an articulation assembly 38. The articulation assembly 38 includes an articulation lever 42 supported on the rotation knob 36. The rotation knob 36 is coupled to the handle assembly 12 and supports the elongate body 14 to facilitate rotation of the elongate body 14 and the tool assembly 16 about the longitudinal axis "X" in relation to the handle assembly 12.

The tool assembly 16 is secured to the distal portion 14b of the elongate body 14 by a pivot member 44 that defines an axis "Y" that is transverse to the longitudinal axis "X". The articulation lever 42 is operatively coupled to the tool assembly 16 via an articulation linkage (not shown) such that manipulation of the articulation lever 42 causes articulation of the tool assembly 16 about the axis "Y" between a non-articulated position in which the tool assembly 16 is aligned with the longitudinal axis "Y" and articulated positions in which a longitudinal axis of the tool assembly and the longitudinal axis "X" define acute angles.

The tool assembly 16 includes a cartridge assembly 48 and an anvil assembly 50. The cartridge assembly 48 includes a channel 52 that supports a staple cartridge 54. In aspects of the disclosure, the staple cartridge 54 is removably received in the channel 52 and can be replaced after each firing of the stapling device 10 to facilitate reuse of the stapling device 10. The channel 52 is pivotably coupled to the anvil assembly 50 and is movable in relation to the anvil assembly 50 between unclamped and clamped positions.

Figure 2:
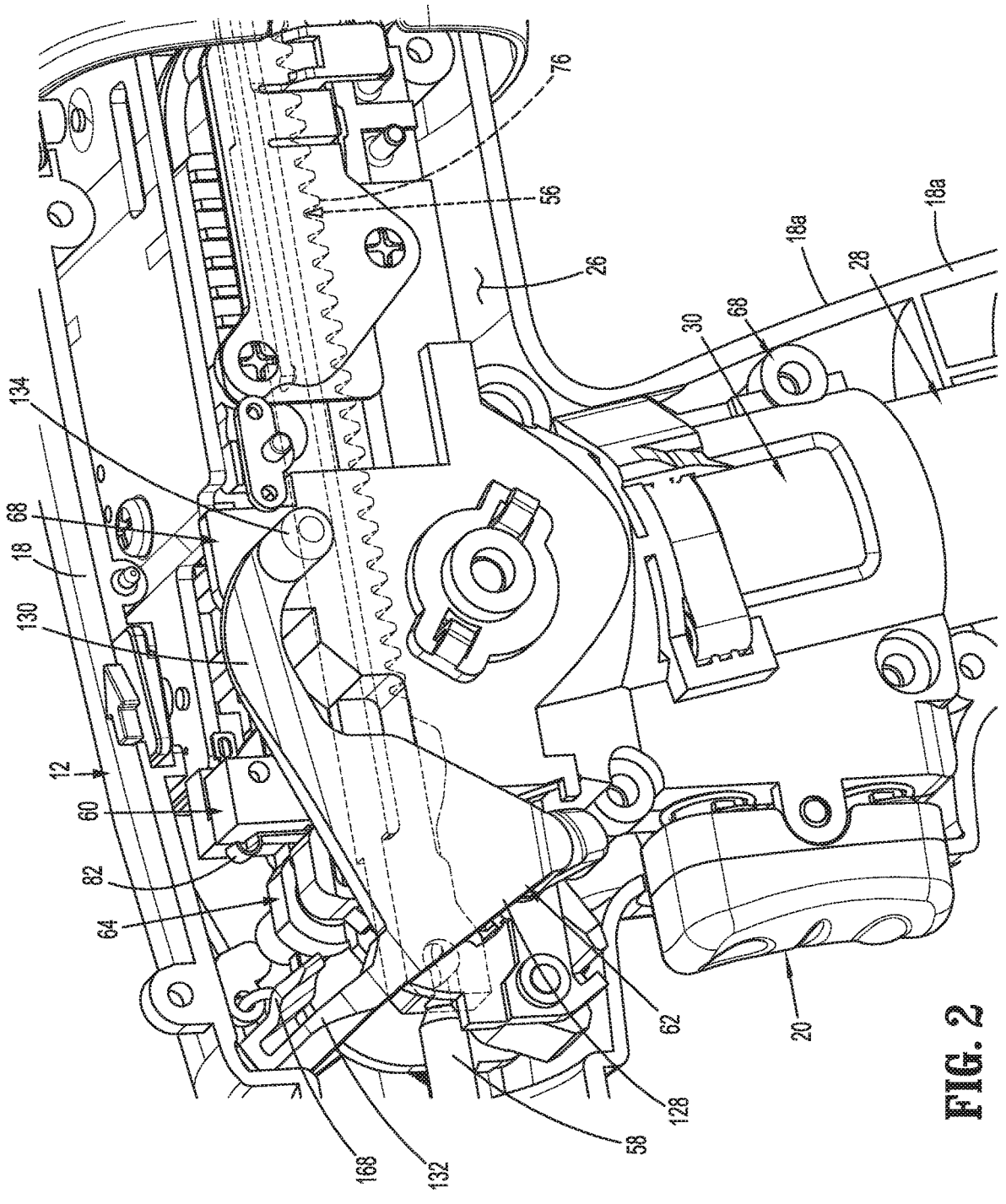
FIG. 2 is an enlarged view of the indicated area of detail shown in FIG. 1 with a section of the outer housing of the handle assembly removed to expose internal components of the handle assembly.
Figure 3:
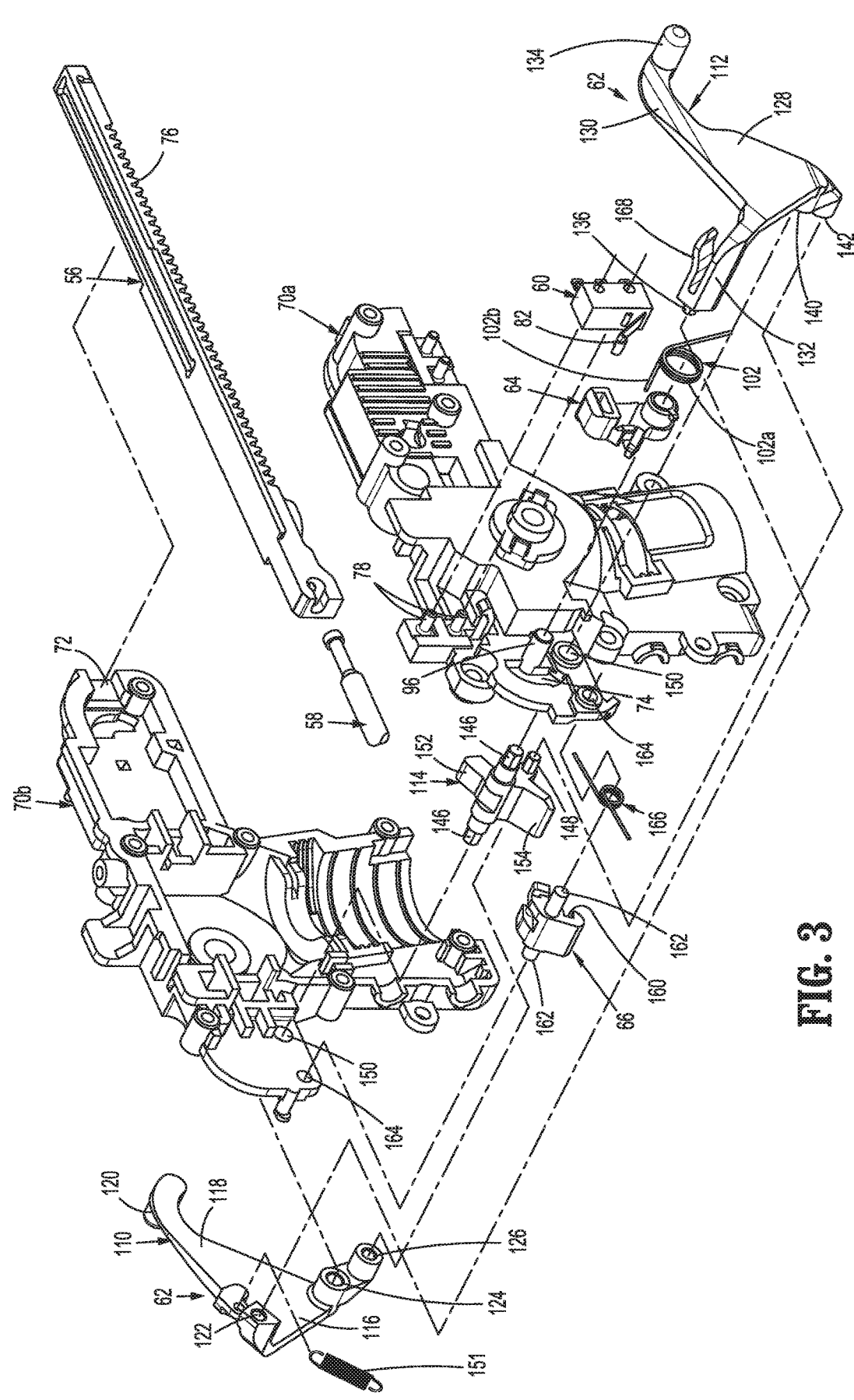
FIG. 3 is an exploded view of some of the internal components of the handle assembly of the surgical device shown in FIG. 2 including a safety trigger assembly, a bias arm, and a safety hook.

FIGS. 2 and 3 illustrate internal components of the handle assembly 12 which includes a rack 56, a control rod 58, a safety switch 60, a safety trigger assembly 62, a bias arm 64, a latch 66, and an inner housing assembly 68 (FIG. 2). The inner housing assembly 68 is formed from left and right half-sections 70a and 70b, respectively and is secured within the outer housing 18 with screws or the like (not shown) to support the internal components of the handle assembly 12 (FIG. 1). The inner housing assembly 68 defines a channel 72 (FIG. 3) that receives and supports the rack 56 for linear movement between rack retracted and advanced positions. The left half-section 70a of the inner housing assembly 68 defines a window 74 that is positioned adjacent the channel 72. The control rod 58 is rotatably coupled to a distal portion of the rack 56 and extends through the elongate body 14 to the tool assembly 12 (FIG. 1). The control rod 58 is movable between rod retracted and advanced positions in response to movement of the rack between the rack's advanced and retracted positions to actuate the tool assembly 12, i.e., move the tool assembly 12 from the unclamped to the clamped positions and fire the stapling device. The rack 56 includes teeth 76 that are engaged with the motor/gear assembly 30 such that activation of the motor/gear assembly 30 moves the rack 56 within the channel 72.

The safety switch 60 is supported on an outer surface of the inner housing assembly 68 and electrically couples the batteries 28 (FIG. 2) to the motor/gear assembly 30. When the safety switch 60 is in an open condition, power to the motor/gear assembly 60 is disrupted. In aspects of the disclosure, the left half-section 70a of the inner housing assembly 68 includes posts 78 (FIG. 3) that are received within openings 80 in the safety switch 60 to support the safety switch 60 on the inner housing assembly 68. It is envisioned that the safety switch 60 may be supported within the outer housing 18 (FIG. 1) of the handle assembly 12 in a variety of different manners. In some aspects of the disclosure, the safety switch 60 includes a micro-switch that has a hinge lever 82 that is normally positioned such that the safety switch 60 is in a first state. The hinge lever 82 is deformable as described in further detail below to move the safety switch 60 to a second state to enable activation of the motor/gear assembly 30 (FIG. 2) via the actuation button 20 (FIG. 1). When the safety switch 60 is in the open position, the motor gear assembly 30 is disabled. When the safety switch 60 is in the second state, the actuation button 20 can be depressed to initiate clamping or firing of the stapling device 10 (FIG. 1).

Figures 4, 5:
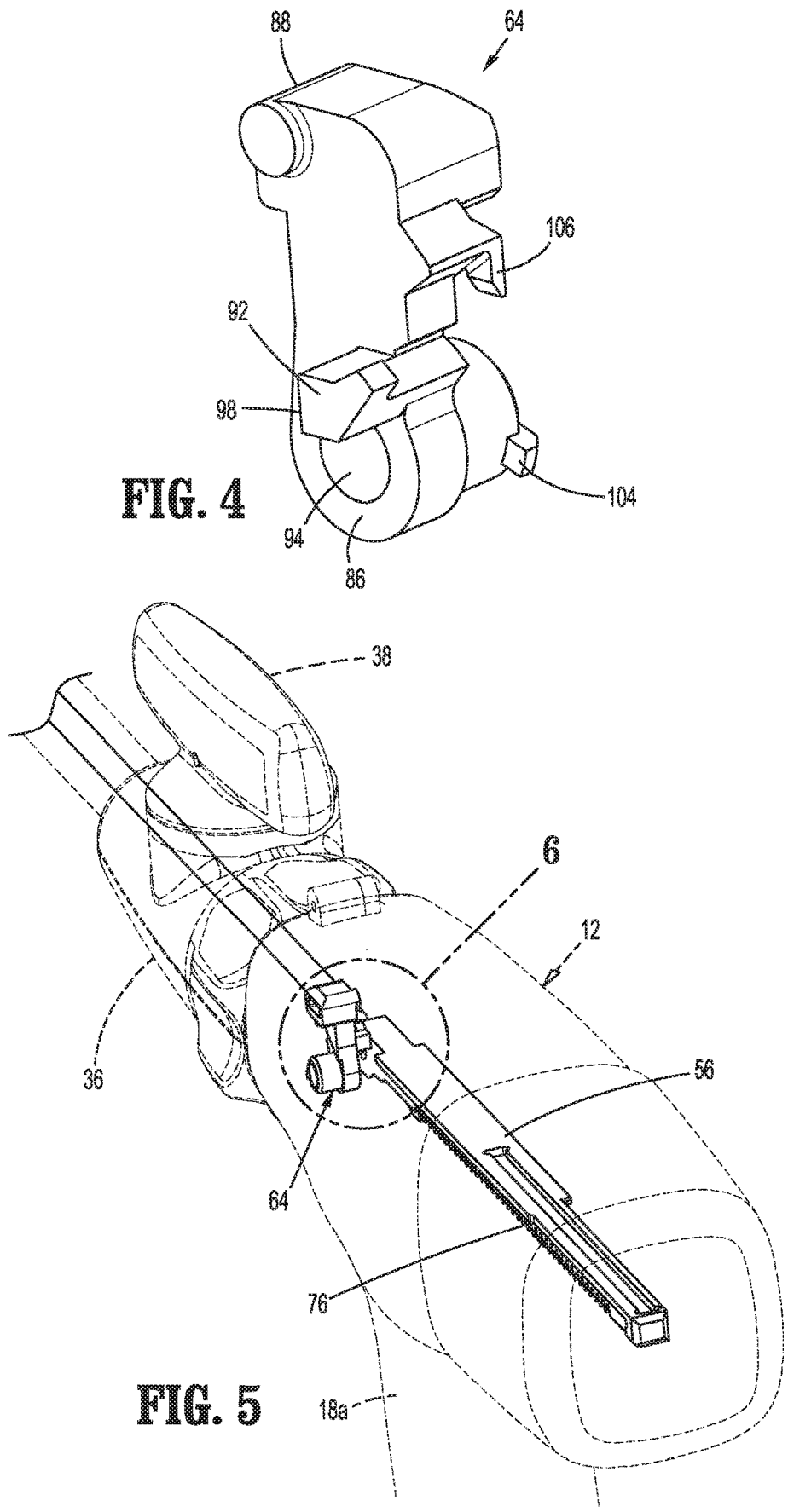
FIG. 4 is a side perspective view of the bias arm of the handle assembly shown in FIG. 3.
FIG. 5 is a perspective view from the proximal end of the rack, drive rod, and bias arm of the stapling device shown in FIG. 1 in an assembled state with the outer housing of the handle assembly and portions of the adapter assembly shown in phantom in an initial position of the stapling device.
Figure 6:
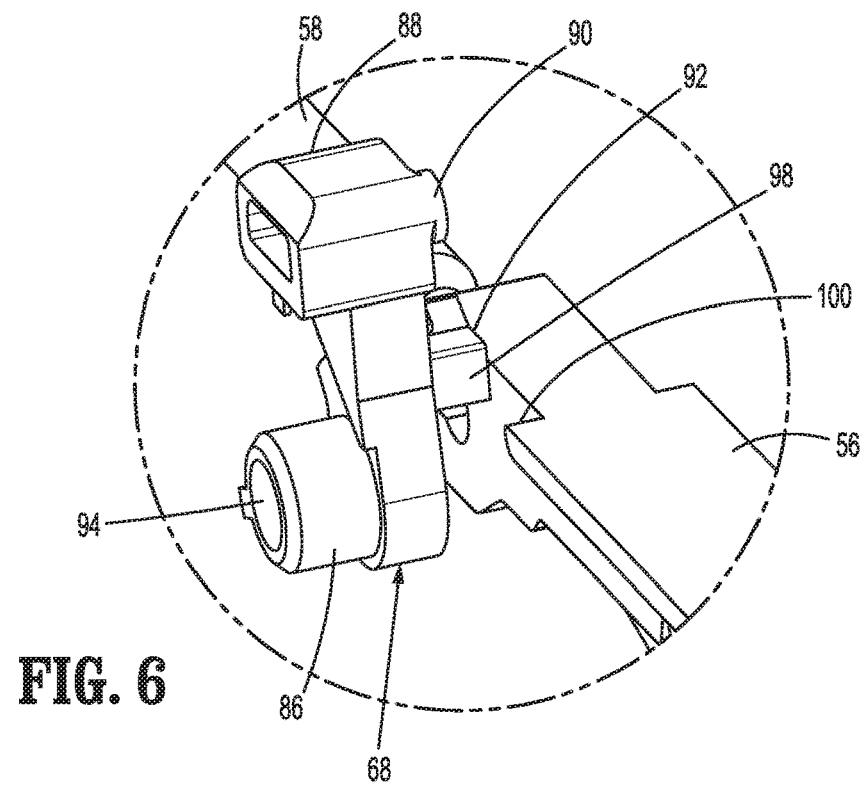
FIG. 6 is an enlarged view of the indicated area of detail shown in FIG. 5.

FIGS. 3 and 4 illustrate the bias arm 64 which is pivotally supported on an outer surface of the inner housing assembly 68 adjacent to the safety switch 60. The bias arm 64 includes a body having a hub 86, an abutment member 88, and a cam member 92. The hub 86 defines a cylindrical opening 94 that receives a post 96 formed on the inner housing assembly 68 to pivotably secure the bias arm 68 about a pivot axis defined by the post 96 to the inner housing assembly 68. The bias arm 64 is pivotable in relation to the inner housing assembly 68 from a first position to a second position. In the first position of the bias arm 64, the abutment member 88 of the bias arm 68 is engaged with the hinge lever 82 of the safety switch 60 to position the safety switch 60 in the second state. In the second position of the bias arm 64, the abutment member 88 of the bias arm 68 is moves away from the safety switch 60 to allow the hinge lever 82 of the safety switch 60 to return to an undeformed position to allow the safety switch 60 to change to the first state.

FIGS. 3, and 5-9 illustrate the bias arm 64 in association with the rack 56. The cam member 92 of the bias arm 64 extends through the window 74 in the inner housing assembly 68 into the channel 72 of the inner housing assembly 68 and into the path of the rack 56. In aspects of the disclosure, the cam member 92 includes a proximal surface 98 that is aligned with a shoulder 100 (FIG. 6) of the rack 56. When the rack 56 moves from the rack retracted position towards the rack advanced position to move the tool assembly 16 (FIG. 1) to a clamped position, the shoulder 100 of the rack 56 engages proximal surface 98 of the cam member 92 to pivot the bias arm 64 from the first position to the second position to allow the safety switch 60 to change to the first state. In the first state of the safety switch 60, power to the motor/gear assembly 30 (FIG. 2) is disrupted. The bias arm 64 is urged to the first position by a biasing member 102. In aspects of the disclosure, the biasing member 102 includes a torsion spring that is positioned about the hub 86 of the bias arm 64 to urge the bias arm 64 to the first position. Alternately, it is envisioned that the bias arm 64 could be urged towards the first position using a variety of different types of biasing members. In aspects of the disclosure, the hub 86 of the bias arm 64 includes a tab 104 that retains a circular portion 102a (FIG. 3) on the hub 64 and a finger 106 that supports an arm 102b of the biasing member 102.

Figure 7:
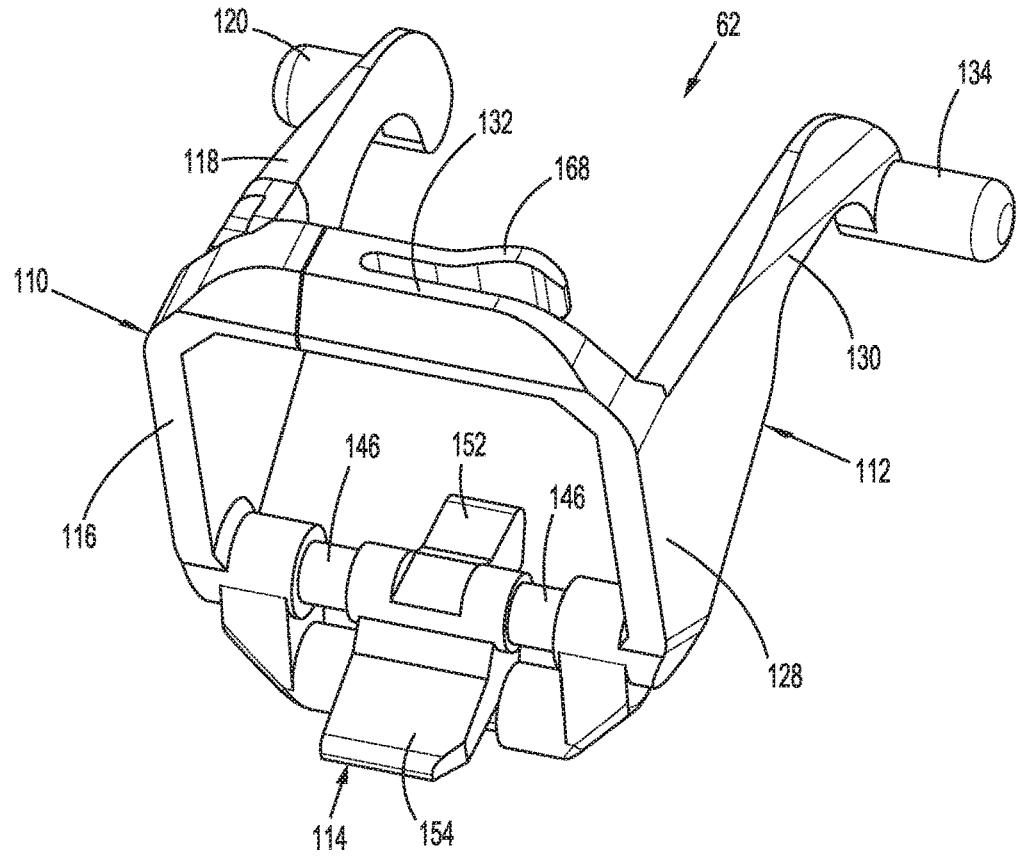
FIG. 7 is a perspective view from a distal end of the safety trigger assembly of the handle assembly shown in FIG. 3.
Figure 8:
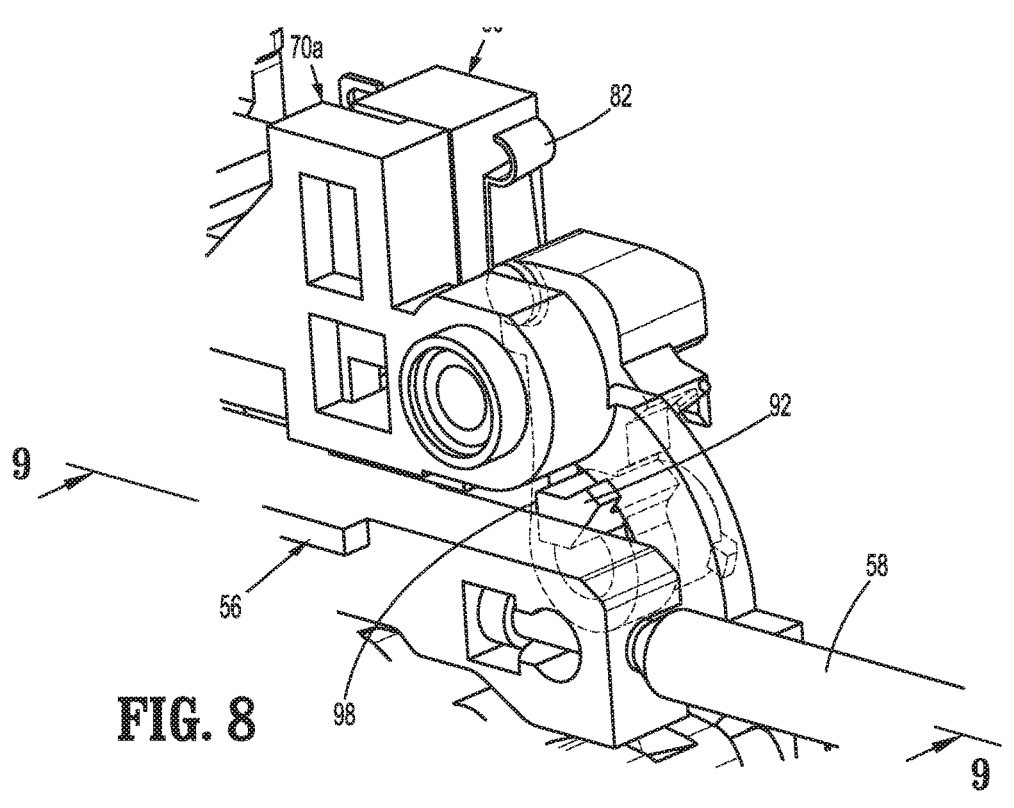
FIG. 8 is a side perspective view of some of the internal components of the handle assembly of the surgical device shown in FIG. 2 including a first half-section of an inner housing, a switch, the bias arm, the rack, and the drive rod with the stapling shown in FIG. 1 in the unclamped, pre-fired position.

FIGS. 3 and 7 illustrate the safety trigger assembly 62. The safety trigger assembly 62 includes a first trigger member 110, a second trigger member 112, and a retainer member 114 that are coupled together to form a unitary assembly. The first and second trigger members 110 and 112 are supported on opposite sides of the inner housing assembly 68, and the retainer member 114 is supported between the left and right half-sections 70a and 70b of the inner housing assembly 68.

The first trigger member 110 includes a body 116 and an arm 118 that extends proximally from the body 116. The arm 118 includes a safety button 120 that extends outwardly from the arm 118 and through the curved slot 32 of the outer housing half-section 22. The body 116 (FIG. 3) of the first trigger member 110 defines a first bore 122, a second bore 124, and a third bore 126.

The second trigger member 112 includes a body 128 and an arm 130 that extends proximally from the body 128, and a transverse portion 132. The arm 130 includes a safety button 134 that extends outwardly from the arm 130 and through the curved slot 32 (FIG. 1) of the outer housing half-section 24 (FIG. 1). The transverse portion 132 includes a post 136 (FIG. 3) that is received within the first bore 122 of the first trigger member 110 to secure the second trigger member 112 to the first trigger member 110. The body 128 of the second trigger member 112 defines first and second bores 140 and 142 (FIG. 3).

Figures 12, 13:
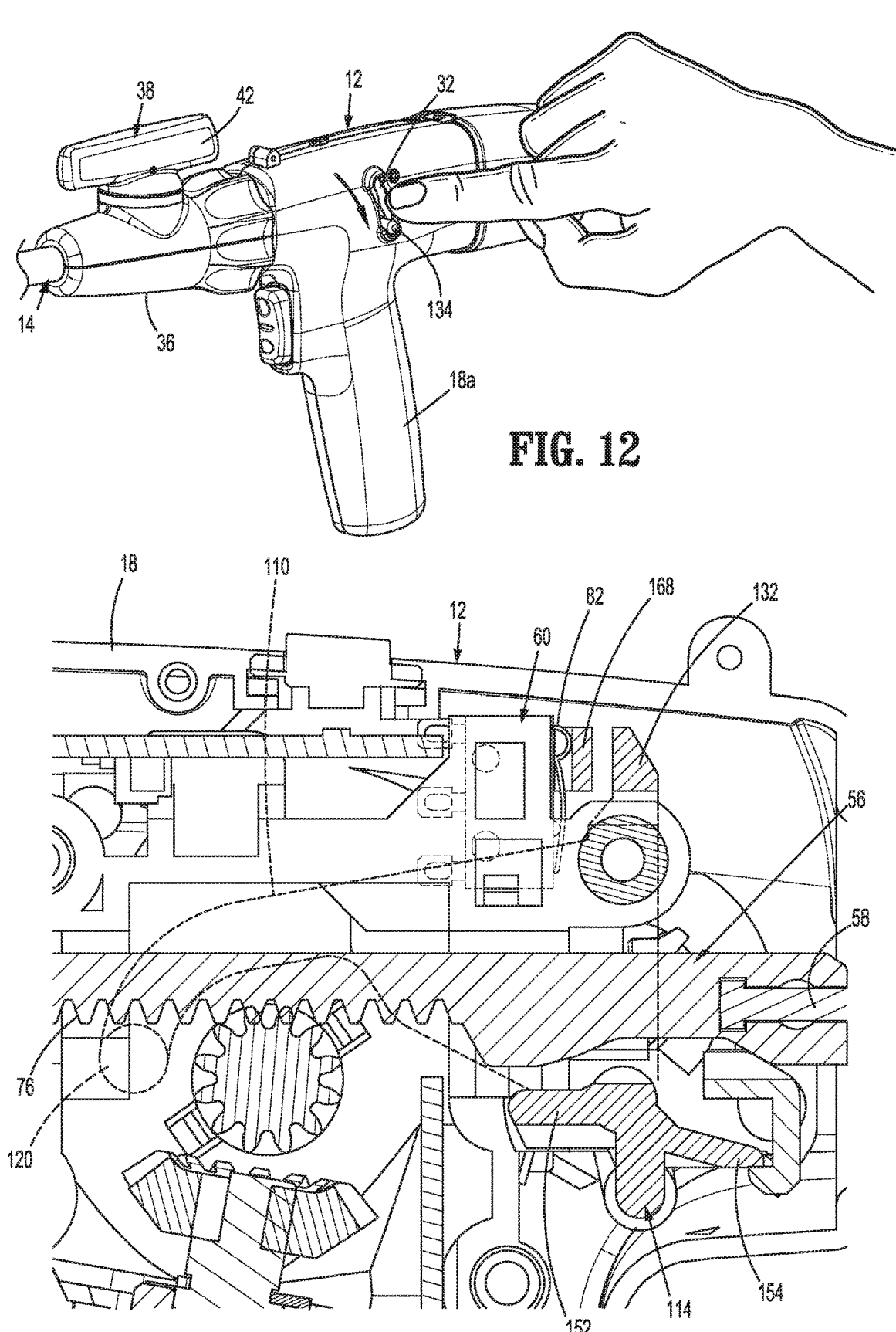
FIG. 12 is a side perspective view of the handle portion of the surgical device shown in FIG. 9 with the safety trigger assembly moved to a fire-ready position.
FIG. 13 is a cross-sectional view taken through a portion of the handle assembly shown in FIG. 12 with the safety trigger assembly in the fire-ready position.
Figure 14:
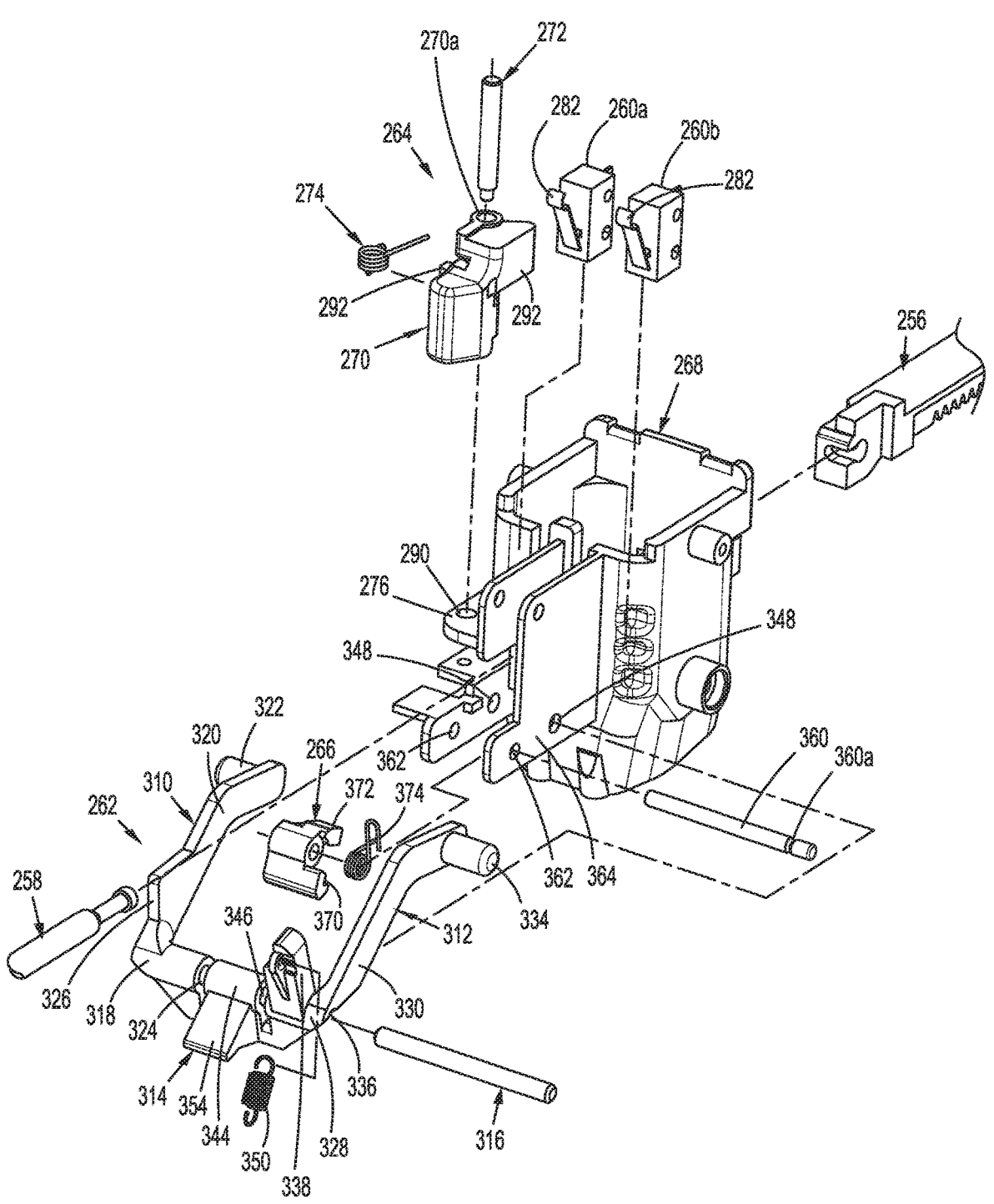
FIG. 14 is an exploded view of internal components of an alternate version of the handle assembly of the stapling device shown in FIG. 1 illustrating alternate versions of the safety trigger assembly, the bias arm assembly, the inner housing, the rack, and the control rod.

The retainer member 114 includes a central body portion 144 and upper and lower posts 146 and 148 that extend outwardly from each side of the central body portion 144. The upper posts 146 extend through openings 150 formed in the left and right half-sections 70a and 70b of the inner housing assembly 68 and are received within the openings 124 and 140 of the first and second trigger members 110 and 112 to pivotally secure the safety trigger assembly 62 to the inner housing assembly 68. The lower posts 148 of the retainer member 114 extend into the openings 126 and 142 of the first and second trigger members 110 and 112. The retainer member 114 secures the first and second trigger members 110 and 112 together such that the retainer member 114 and the first and second trigger members 110 and 112 form the safety trigger assembly 62 (FIG. 7). The safety trigger assembly 62 is pivotable about a transverse axis defined by the upper posts 146 from a safe position (FIG. 1), through an intermediate position (FIG. 10), to a fire-ready position (FIG. 12).

The safety trigger assembly 62 includes a biasing member 151 (FIG. 3) that is coupled to the housing 18 of the handle assembly 12 and to the first trigger member 110 to urge the safety trigger assembly 62 to the safe position (FIG. 1). In aspects of the disclosure, the biasing member 151 includes a coil spring although the use of other types of biasing members is envisioned.

Figure 9:
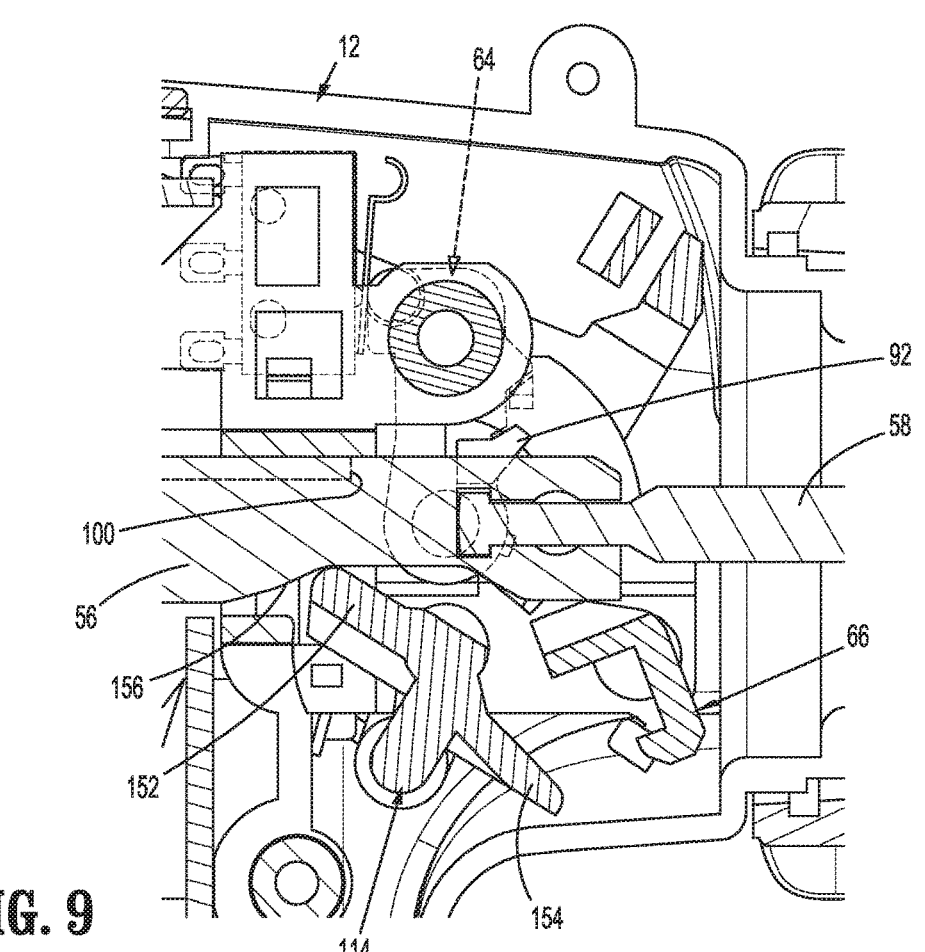
FIG. 9 is a cross-sectional view taken along section line 9-9 of FIG. 8.

The central body portion 144 of the retainer member 114 includes a proximally extending cam member 152 and a distally extending finger 154. The cam member 152 engages a bottom surface of the rack 56 (FIG. 9). The bottom surface of the rack 56 defines a cam surface 156 (FIG. 9) that is configured to pivot the safety trigger assembly 62 from the safe position (FIG. 1) to the intermediate position (FIG. 10) when the stapling device 10 (FIG. 1) is moved to the clamped position. The finger 154 is positioned to engage the latch 66 to retain the safety trigger assembly 62 in the fire-ready position as described below.

The latch 66 includes a body that defines a pocket 160 and includes outwardly extending posts 162. The posts 162 are received within openings 164 defined in the left and right half-sections 70a and 70b of the inner housing assembly 68 to pivotably secure the latch 66 to the inner housing assembly 68. The latch 66 is pivotable between a latched position (FIG. 11) and an unlatched position (FIG. 9). The latch 66 is urged by a biasing member 166 (FIG. 3) towards the latched position. In aspects of the disclosure, the biasing member 166 includes a torsion spring although the use of other types of biasing members is envisioned. When the stapling device 10 (FIG. 1) is in the unclamped, pre-fired position, the latch 66 is retained in the unlatched position by the bottom surface of the rack 56 (FIG. 9). As described below, when the rack 56 moves from the rack retracted position towards the rack advanced position, the contour of the bottom surface of the rack 56 allows the biasing member 166 to move the latch 66 to the latched position.

When the safety trigger assembly 62 is moved from the safe position towards the fire-ready position, the transverse portion 132 of the second trigger member 112 is positioned to pass over the inner housing assembly 68 and the bias arm 64 into engagement with the hinge lever 82 of the safety switch 60. In aspects of the disclosure, the transverse portion 132 of the second trigger member 112 includes a spring arm 168 that engages the hinge lever 82 of the safety switch 60 when the safety trigger assembly 62 is in the fire-ready position.

FIG. 9 illustrates the handle assembly 12 in an unclamped, pre-fired position. In this position, the shoulder 100 of the rack 56 is positioned proximally of the cam member 92 of the bias arm 64 such that the biasing member 102 (FIG. 3) urges the abutment member 88 of the bias arm 64 into the hinge lever 82 of the safety switch 60 to move the safety switch 60 to the second state. In the second state, the actuation button 20 (FIG. 1) can be depressed to actuate the stapling device 10 (FIG. 1) to move the stapling device 10 from the unclamped position to the clamped position. As illustrated in FIG. 1, the safety button 134 of the safety trigger assembly 62 is shielded by the safety button shield 34 when the safety trigger assembly 62 is in the safe position.

Figure 10:
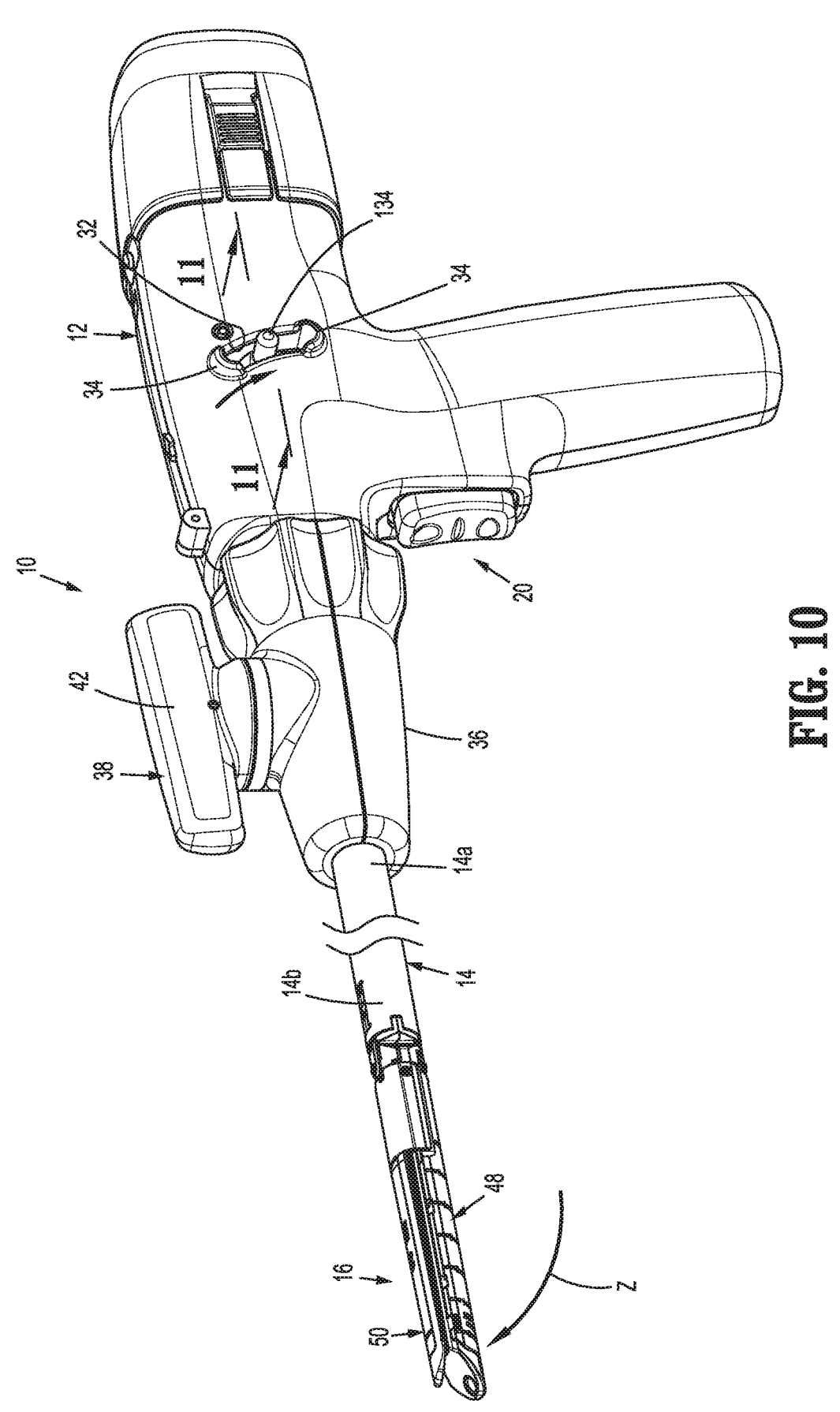
FIG. 10 is a side perspective view of the surgical device shown in FIG. 1 in a clamped position with the safety trigger assembly in an intermediate position.
Figure 11:
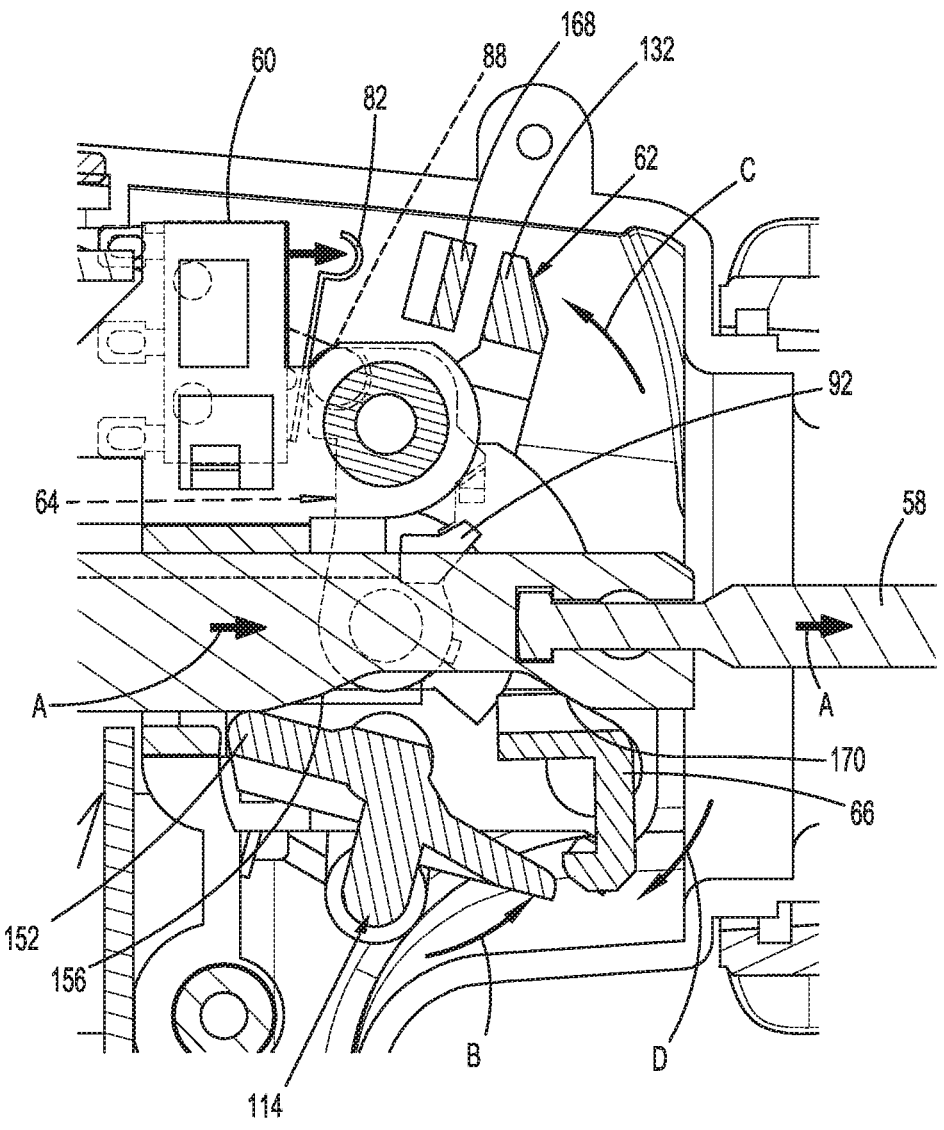
FIG. 11 is a cross-sectional view taken along section line 11-11 of FIG. 10.

FIGS. 10 and 11 illustrate the stapling device 10 in the clamped, pre-fired position. When the stapling device 10 is moved to the clamped position by pressing the actuation button 20, the rack 56 and the control rod 58 move in the direction indicated by arrow "A" in FIG. 11 from the rack/control rod retracted position to a rack/control rod clamped position. As the rack 56 moves in the direction of arrow "A", the cam surface 156 on the bottom of the rack 56 engages the cam member 152 of the retainer member 114 of the safety trigger assembly 62 and pivots the retainer member 114 in the direction of arrow "B" in FIG. 11. As described above, the retainer member 114 is fixedly coupled to the first and second trigger members 110 and 112 such that the entire safety trigger assembly 62 including the transverse portion 132 of the second trigger member 112 pivots with the retainer member 114 in the direction of arrow "C" in FIG. 11 to the intermediate position. In the intermediate position, the safety buttons 120 and 134 of the safety trigger assembly 62 are moved within the curved slots 32 to an exposed position spaced from the safety button shields 34. It is also noted that the latch 66 which is engaged with the bottom surface of the rack 56 moves within a cavity 170 defined in the bottom surface of the rack 56 and is pivoted in the direction of arrow "D" in FIG. 11 to the latched position by the biasing member 166.

Although not described in detail herein, upon advancement of the rack 56 from the rack retracted position to the rack clamped position, the cartridge assembly 48 pivots towards the anvil assembly 50 in the direction of arrow "Z" in FIG. 10 to move the tool assembly to the clamped position.

When the rack 56 moves from the rack retracted position (FIG. 9) to the rack clamped position (FIG. 11), the shoulder 100 on the rack 56 moves into engagement with the cam member 92 of the bias arm 64 to pivot the bias arm 64 away from the safety switch 60 in the direction of arrow "E" in FIG. 11 to allow the safety switch 60 to move to the first state. As described above, when the safety switch 60 is in the first state, power is disrupted to the motor/gear assembly 30 (FIG. 2) and advancement of the rack 56 stops in the rack clamped position.

FIGS. 12 and 13 illustrate the stapling device 10 when the safety trigger assembly 62 is moved from the intermediate position (FIG. 9) to the fire-ready position (FIG. 12). To move the safety trigger assembly 62 from the intermediate position to the fire-ready position, a clinician engages one or both the safety buttons 120 and 134 (only safety button 134 is shown) and slides the safety buttons 120 and 134 downwardly within the curved slots 32 of the outer housing 18. When the safety buttons 120 and 134 are slid downwardly within the curved slots 32, the safety trigger assembly 62 rotates within the outer housing 18 of the handle assembly 12 in the direction of arrow "F" such that the spring arm 168 on the transverse portion 132 of the second trigger member 112 moves into engagement with the hinge lever 82 of the safety switch 60 to move the safety switch 60 to the second state and the retainer member 114 pivots in the direction of arrow "G" to move the finger 154 of the retainer member 114 into engagement with the latch 66 to secure the safety trigger assembly 62 in the fire-ready position. When the safety trigger assembly 62 is in the fire-ready position, the safety switch 60 is in the second state and the stapling device 10 can be fired by pressing the actuation button 20 (FIG. 12).

Figure 19:
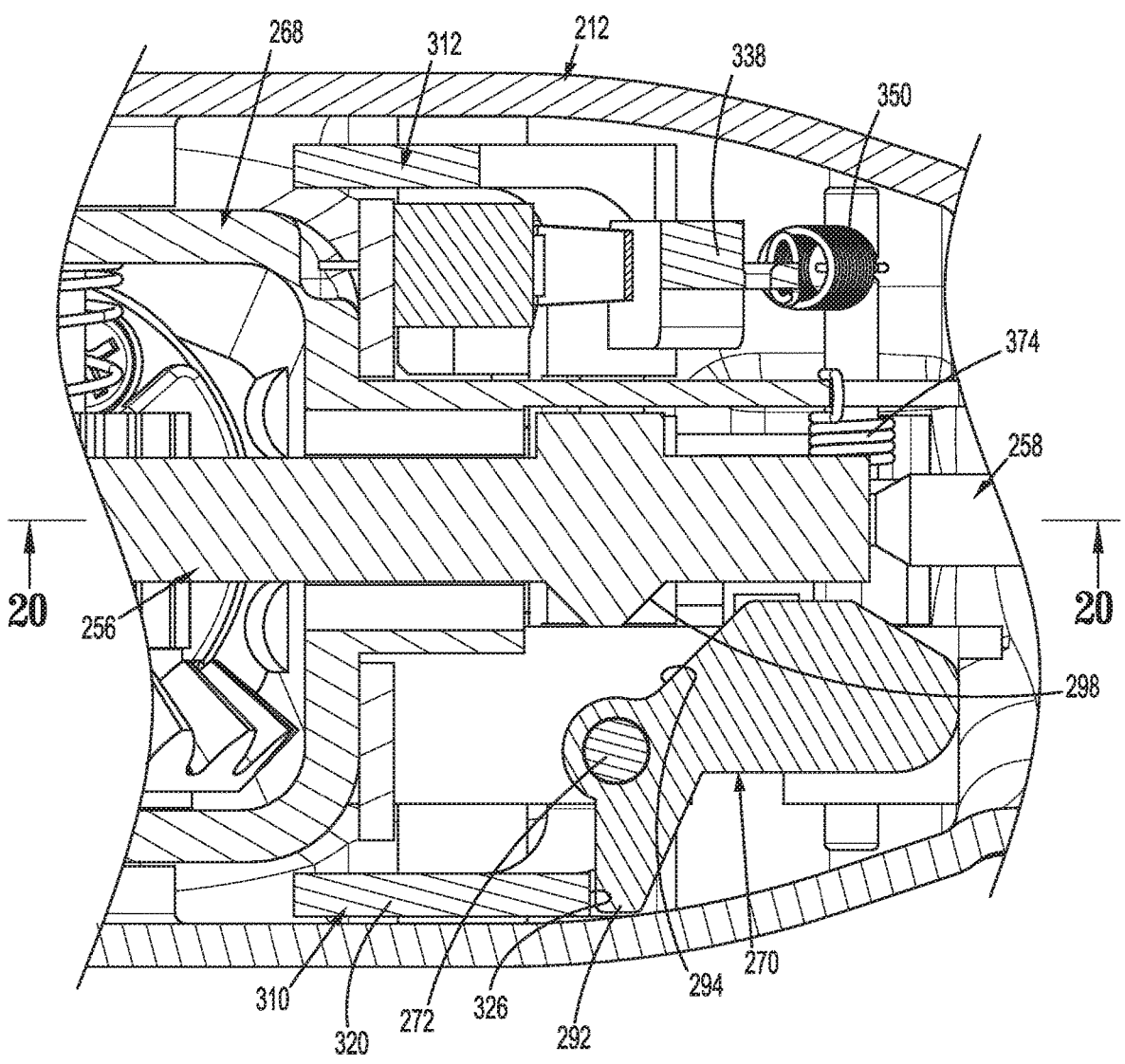
FIG. 19 is a cross-sectional view taken along section line 19-19 of FIG. 15

FIGS. 14-24 illustrate an alternate version of the handle assembly 12 (FIG. 1) of the stapling device 10 (FIG. 1) shown generally as handle assembly 212 (FIG. 19). The handle assembly 212 includes internal components shown in FIGS. 14-16 including a rack 256, a control rod 258, an inner housing 268, a safety trigger assembly 262, and a bias arm assembly 264. The rack 256 is coupled to the control rod 258 as described above regarding rack 56 and control rod 58 and is supported for longitudinal movement within a channel (not shown) formed through the inner housing 268. The rack 256 includes teeth 276 that are engaged by the motor/gear assembly 30 (FIG. 2) to drive the rack longitudinally in relating to the inner housing between a rack retracted position and a rack advanced position. As described above regarding the rack 56 and the control rod 58, longitudinal movement of the rack 256 causes corresponding longitudinal movement of the control rod to actuate the tool assembly 16 (FIG. 1).

The handle assembly 212 includes a first safety switch 260*a*, a second safety switch 260*b*, the safety switch assembly 262, the bias arm assembly 264, and a latch 266. The first safety switch 260*a* is secured to one side of the inner housing 268 and the second safety switch 260*b* is secured to an opposite side of the inner housing 268. Each of the first and second safety switches 260*a* and 260*b* include a hinge lever 282 that functions in the same manner as hinge lever 82 (FIG. 3) and is deformable to change the first and second safety switches 260*a* and 260*b* from first states to second states. As described above regarding the safety switch 60, the safety switches 260*a* and 260*b* can be micro-switches.

The bias arm assembly 264 includes a bias arm 270, a pivot pin 272, and a biasing member 274. The bias arm 270 defines a through bore 270*a* that receives the pivot pin 272 to pivotably secure the bias arm 270 to an outer surface of the inner housing 268 at a position adjacent to the first safety switch 260*a*. In aspects of the disclosure, the inner housing 268 includes a first platform 276 that defines an opening 290 that receives one end of the pivot pin 272 to pivotably secure the bias arm 270 to the inner housing 268. The bias arm 270 is pivotable from a first position engaged with the hinge lever 282 of the first safety switch 260*a* to move the first safety switch 260*a* to a second state to a second position in which the safety switch moves to a first state. The bias arm 270 is urged towards the first position by the biasing member 274. In aspects of the disclosure, the biasing member 274 includes a torsion spring although the use of other types of biasing members is envisioned.

Figures 17, 18:
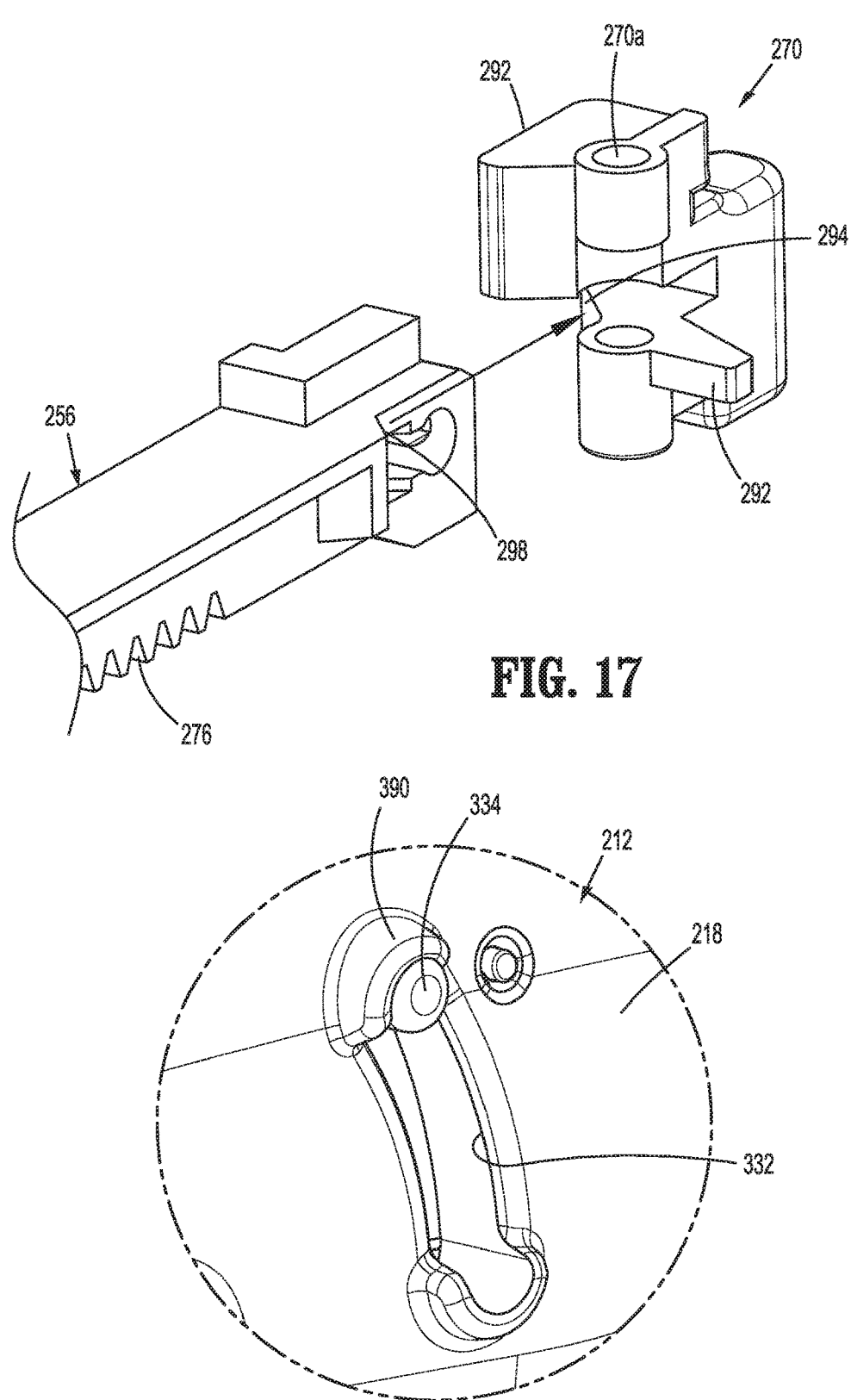
FIG. 17 is a side perspective view of a bias arm of the bias arm assembly and a distal portion of a rack of the handle assembly shown in FIG. 14 with parts separated.
FIG. 18 is an enlarged view of an outer surface of the handle assembly of the stapling device shown in FIG. 1 with the safety trigger assembly in a safe position.

FIG. 17 illustrates the bias arm 270 and a proximal portion of the rack 256. As illustrated, the bias arm 270 of the biasing arm assembly 264 includes an abutment member 292, an activation arm 292, and a cam surface 294. The cam surface 294 is aligned with an angled shoulder 298 formed on the distal portion of the rack 256. When the rack 256 is moved from the rack retracted position towards the rack advanced position to a rack clamped position, the angled shoulder 298 of the rack 256 engages the cam surface 294 of the bias arm 270 to pivot the bias arm 270 from the first position to the second position and allow the first safety switch 260a to change from the second state to the first state. As described above regarding safety switch 60, in the first state, power to the motor/gear assembly 30 (FIG. 2) is disrupted such that advancement of the rack 256 stops when the rack 256 reaches the rack clamped position.

The abutment member 292 of the bias arm 270 is engaged with the safety trigger assembly 262. When the bias arm 270 moves from the first position to the second position upon movement of the rack 256 from the rack retracted position to the rack clamped position, the safety trigger assembly 262 moves from a safe position to an intermediate position as described in further detail below.

The safety trigger assembly 262 includes a first trigger member 310, a second trigger member 312, and a retainer member 314 that are coupled together by a pivot member 316 to form a unitary assembly. The first and second trigger members 310 and 312 are supported on opposite sides of the inner housing 268 and the retainer member 314 is supported between the first and second trigger members.

The first trigger member 310 includes a body 318 and an arm 320 that extends proximally from the body 318. The arm 320 includes a safety button 322 that extends outwardly from the arm 320 and through the curved slot 332 (FIG. 18). The body 318 (FIG. 3) of the first trigger member 310 defines a bore 324 (FIG. 14) that receives the pivot member 316. The arm 320 of the first trigger member 310 includes an engagement surface 326 that is engaged with the abutment member 292 of the bias arm 270.

The second trigger member 312 includes a body 328 and an arm 330 that extends proximally from the body 328. The arm 330 includes a safety button 334 that extends outwardly from the arm 330 and through the curved slot 332 (FIG. 18) of the outer housing half-section 24 (FIG. 1). The body 328 of the second trigger member 112 defines a bore 336 and includes a biasing member mount 338. The bore 336 receives the pivot member 316 to couple the second trigger member 312 to the first trigger member 310 and to the retainer member 314.

The retainer member 314 includes a central body portion 344 that defines a through bore 346 (FIG. 14) that receives the pivot member 316 to fixedly secure the retainer member 314 between the first and second trigger members 310 and 312. Ends of the pivot member 316 are supported in openings 348 formed in the inner housing 268 to pivotably secure the safety trigger assembly 262 to the inner housing 268. The safety trigger assembly 62 is pivotable about a transverse axis defined by the pivot member 316 from a safe position (FIG. 15), through an intermediate position (FIG. 22), to a fire-ready position (FIG. 23). The safety trigger assembly 262 includes a biasing member 350 that is coupled to the biasing member mount 338 and to the inner housing 268 and urges the safety trigger assembly 262 to the safe position. In aspects of the disclosure, the biasing member 350 includes a coil spring although the use of other types of biasing member is envisioned. The central body portion 344 of the retainer member 314 includes a distally extending finger 354 that is positioned to engage the latch 266 to retain the safety trigger assembly 262 in the fire-ready position as described below.

Figures 15, 16:
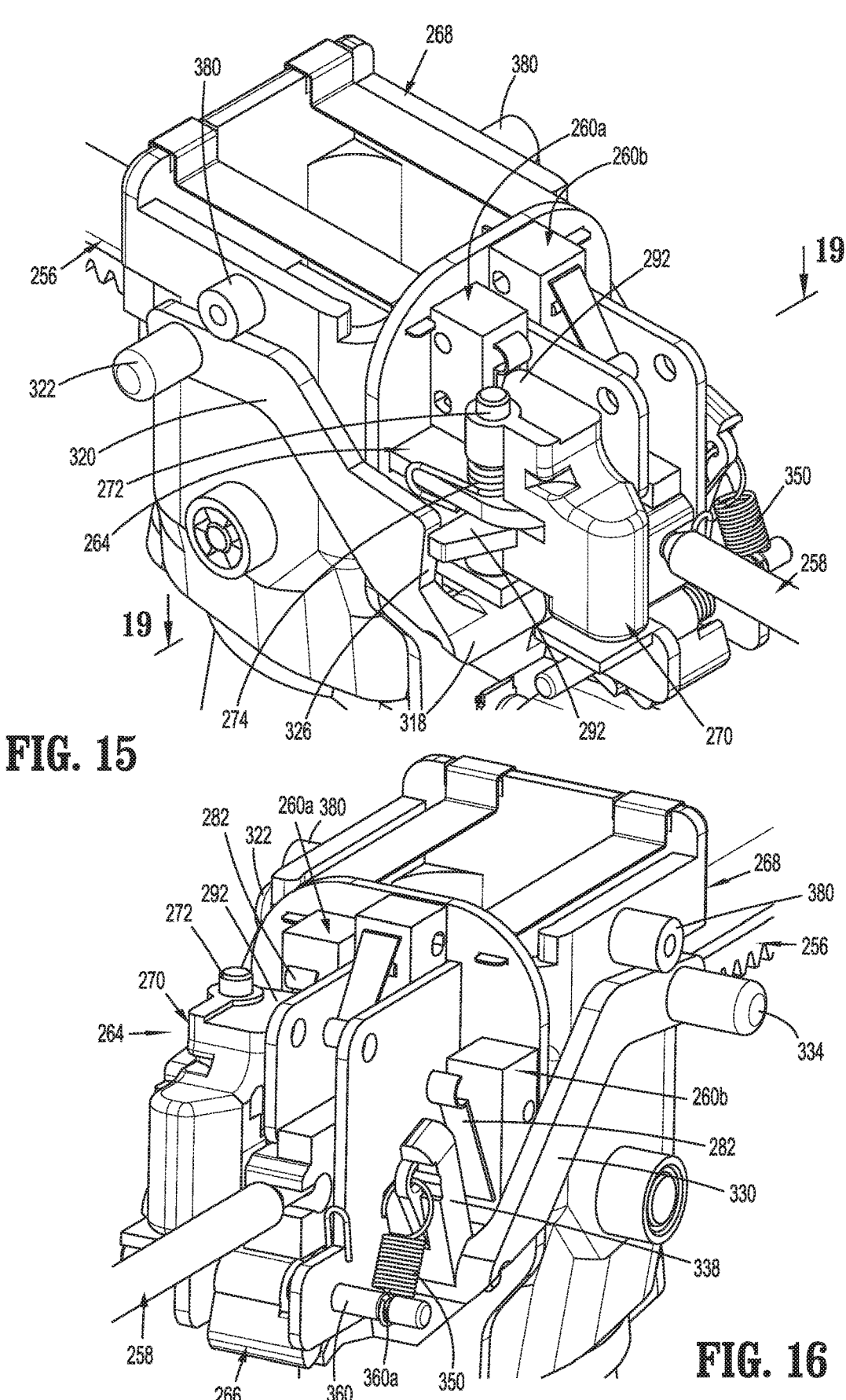
FIG. 15 is a side perspective view from a distal end of the safety trigger assembly and the bias arm assembly shown in FIG. 14 mounted on the inner housing in an unclamped pre-fired position of the stapling device.
FIG. 16 is a side perspective view from a proximal end of the safety trigger assembly and the bias arm assembly shown in FIG. 14 mounted on the inner housing in an unclamped pre-fired position of the stapling device.
Figure 20:
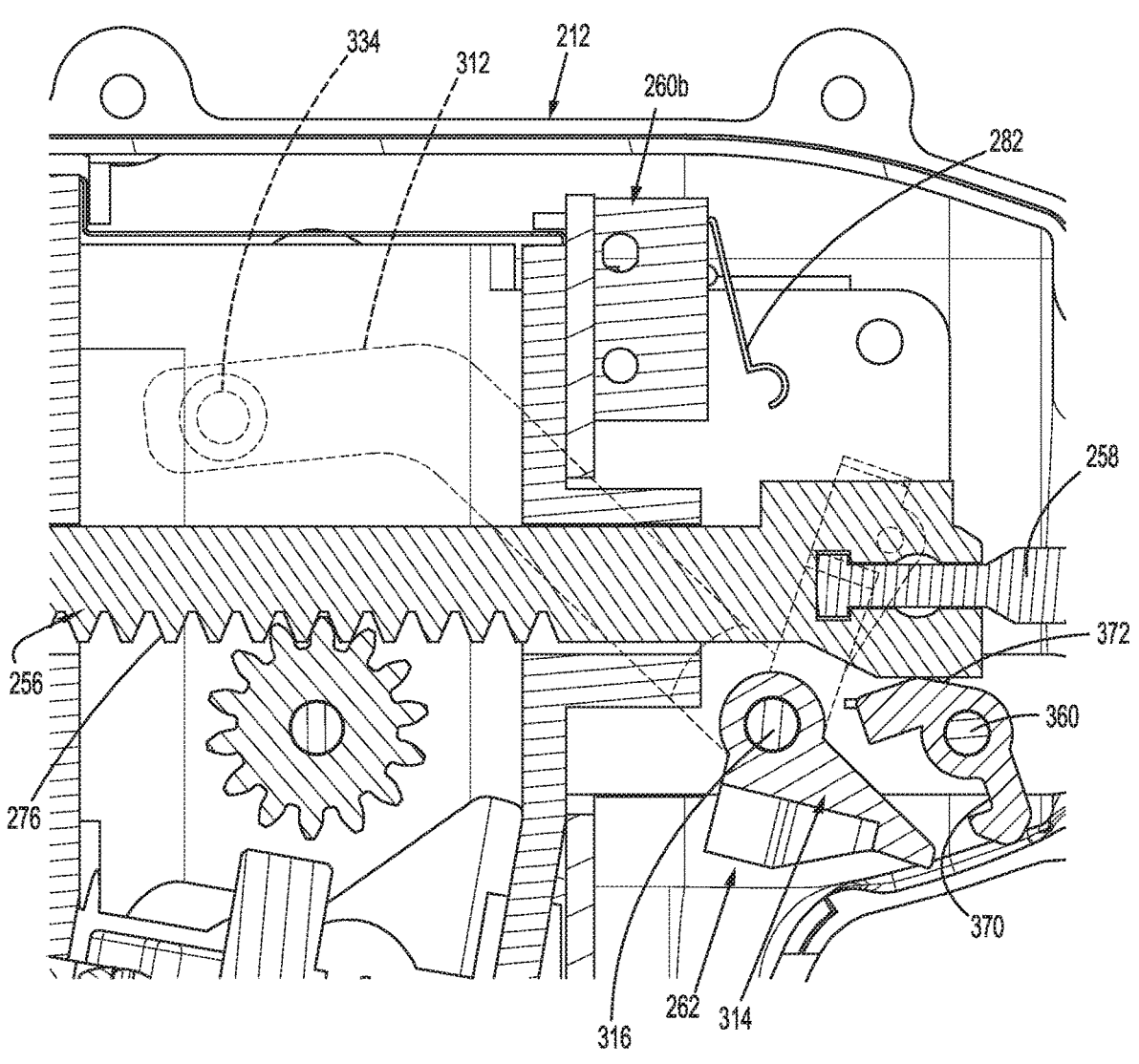
FIG. 20 is a cross-sectional view taken along section line 20-20 of FIG. 19.
Figure 24:
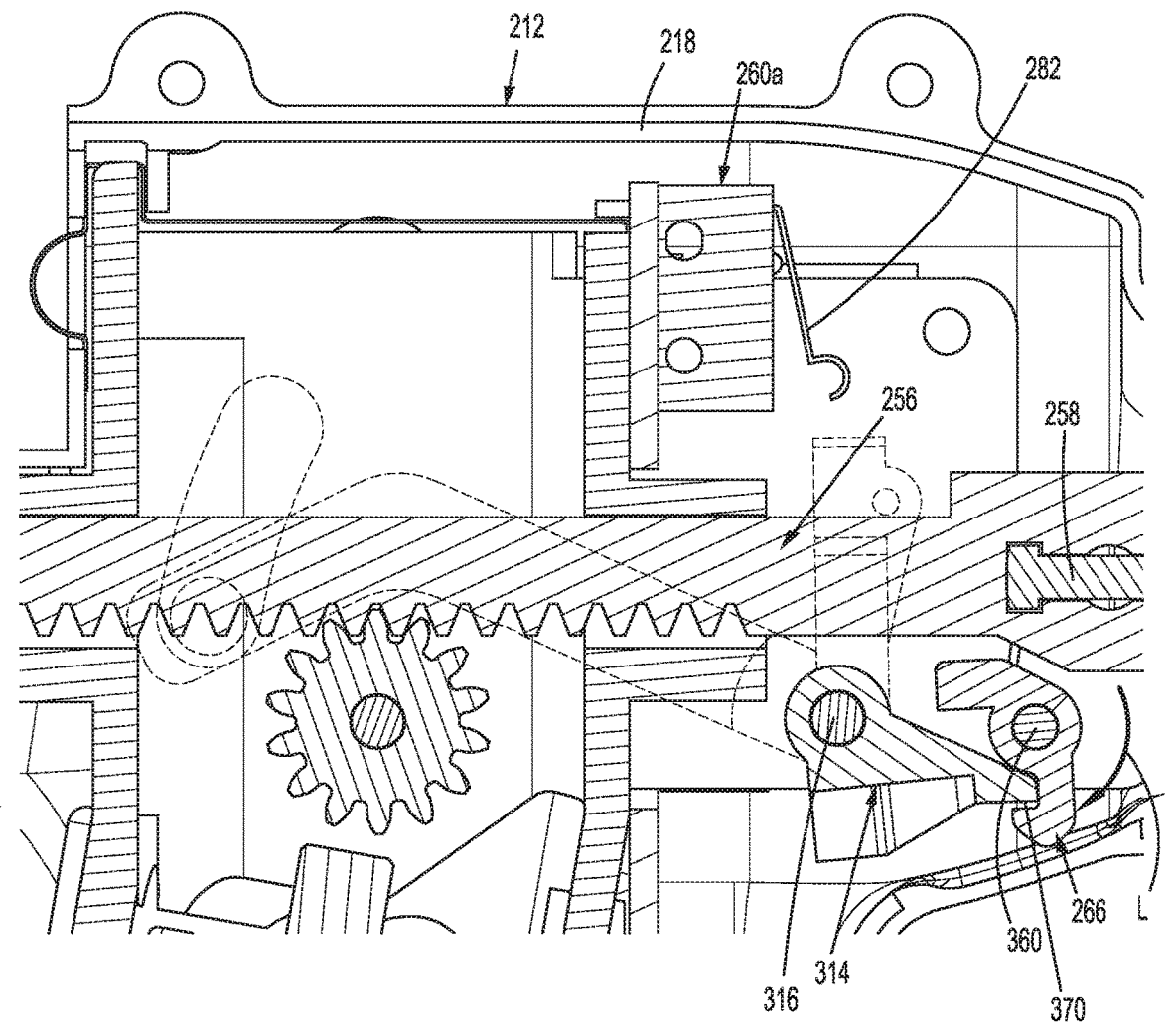
FIG. 24 is a cross-sectional view taken through the handle assembly shown in FIG. 22 in a clamped, pre-fired position of the stapling device with the safety trigger assembly in the fire-ready position.

The latch 266 is pivotably supported within the inner housing 268 by a pivot member 360 (FIG. 14) that extends through openings 362 formed in sidewalls 364 of the inner housing 268. The latch 266 includes a body that defines a pocket 370 and includes a cam surface 372 (FIG. 20). The latch 266 is pivotable in relation to the inner housing 268 between an unlatched position (FIG. 20) and a latched position (FIG. 24). The latch 266 is urged by a biasing member 374 (FIG. 3) towards the latched position. In aspects of the disclosure, the biasing member 374 includes a torsion spring although the use of other types of biasing members is envisioned. When the stapling device 10 (FIG. 1) is in the unclamped, pre-fired position, the cam surface 372 of the latch 266 engages the bottom surface of the rack 256 to retain the latch in the unlatched position. As described below, when the rack 256 moves from the rack retracted position towards the rack advanced position, the contour of the bottom surface of the rack 256 allows the biasing member 374 to move the latch 266 to the latched position. In aspects of the disclosure, one end of the biasing member 350 is secured to the pivot member 360. In some aspects of the disclosure, the pivot member 360 includes an annular recess 360a that receives the end of the biasing member 350 (FIG. 16).

The inner housing 268 includes stop members 380 that extend outwardly from the sidewalls 364 of the inner housing 268 and engage the 320 and 330 of the first and second trigger members 310 and 312 when the safety trigger assembly 262 is in the safe position. The stop members 380 prevent the biasing member 350 from rotating the safety trigger assembly 262 beyond the stop members 380.

FIGS. 18-20 illustrate internal components of the handle assembly 212 when the stapling device 10 is in an unclamped, pre-fired position. In the unclamped, pre-fired position of the stapling device 10, the safety buttons 322 and 334 (FIG. 18—only safety button 334 is shown) of the first and second trigger members 310 and 312 of the safety trigger assembly 262 are positioned in the upper end of the curved slot 332 of the outer housing 218 of the handle assembly 212. In this position, the safety buttons 322 and 334 are shielded by safety button shields 390 (FIG. 18) to prevent inadvertent actuation of the safety trigger assembly 262.

In the unclamped, pre-fired position of the stapling device 10, the rack 256 is in the rack retracted position with the angled shoulder 298 (FIG. 19) of the rack 256 spaced proximally of the cam surface 294 of the bias arm 270 such that the biasing member 274 of the bias arm assembly 264 urges the abutment member 292 of the bias arm 270 into engagement with the hinge lever 282 of the first safety switch 260a to place the first safety switch 260a in the second state. In addition, the cam surface 372 (FIG. 20) of the latch 266 is engaged with the bottom surface of the rack 256 to retain the latch 266 in the unlatched position. As described above, when the first safety switch 260a is in the second state, the actuation button 20 (FIG. 1) of the handle assembly can be actuated to activate the motor/gear assembly 30 (FIG. 2) and move the stapling device 10 (FIG. 1) from the unclamped to the clamped position.

Figure 21:
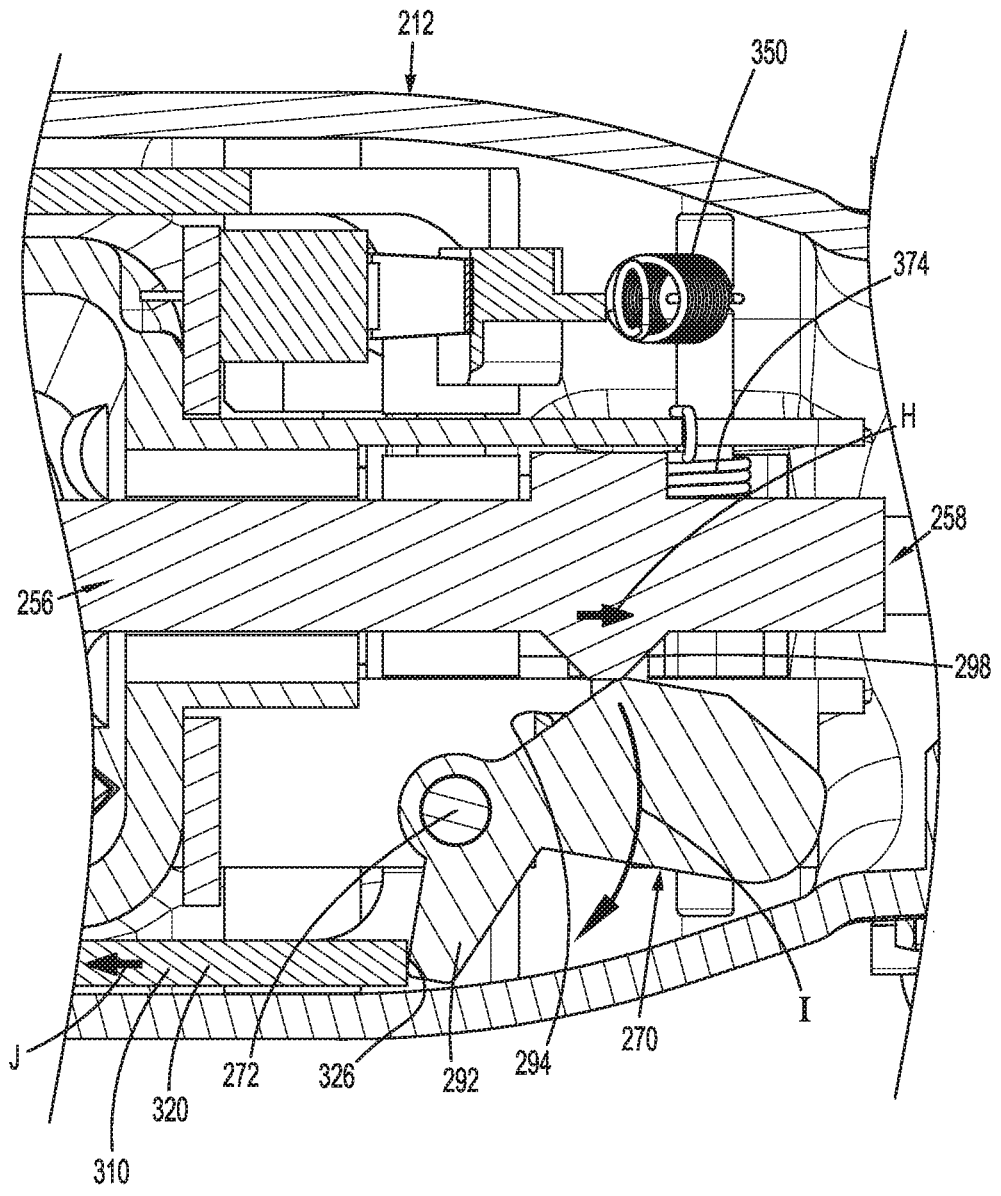
FIG. 21 is a cross-sectional view taken through the alternate version of the handle assembly of the stapling device shown in FIG. 1 with the rack in a rack clamped position and the safety trigger assembly in an intermediate position.
Figure 22:
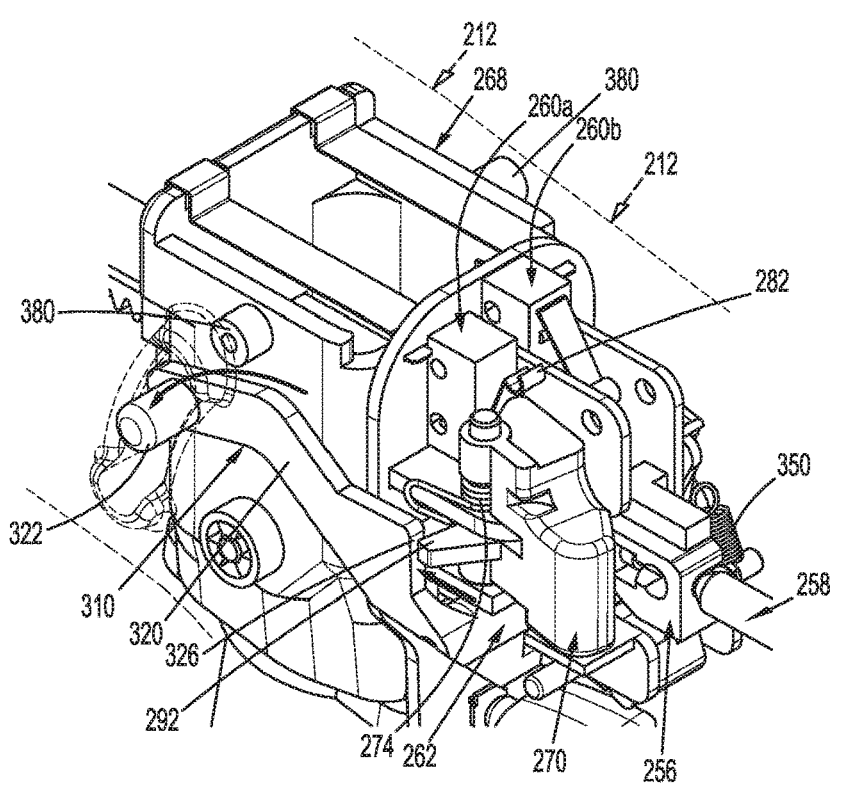
FIG. 22 is a side perspective view from the distal end of the internal components of the handle assembly shown in FIG. 15 in a clamped, pre-fired position of the stapling device with the safety trigger assembly in an intermediate position.
Figure 23:
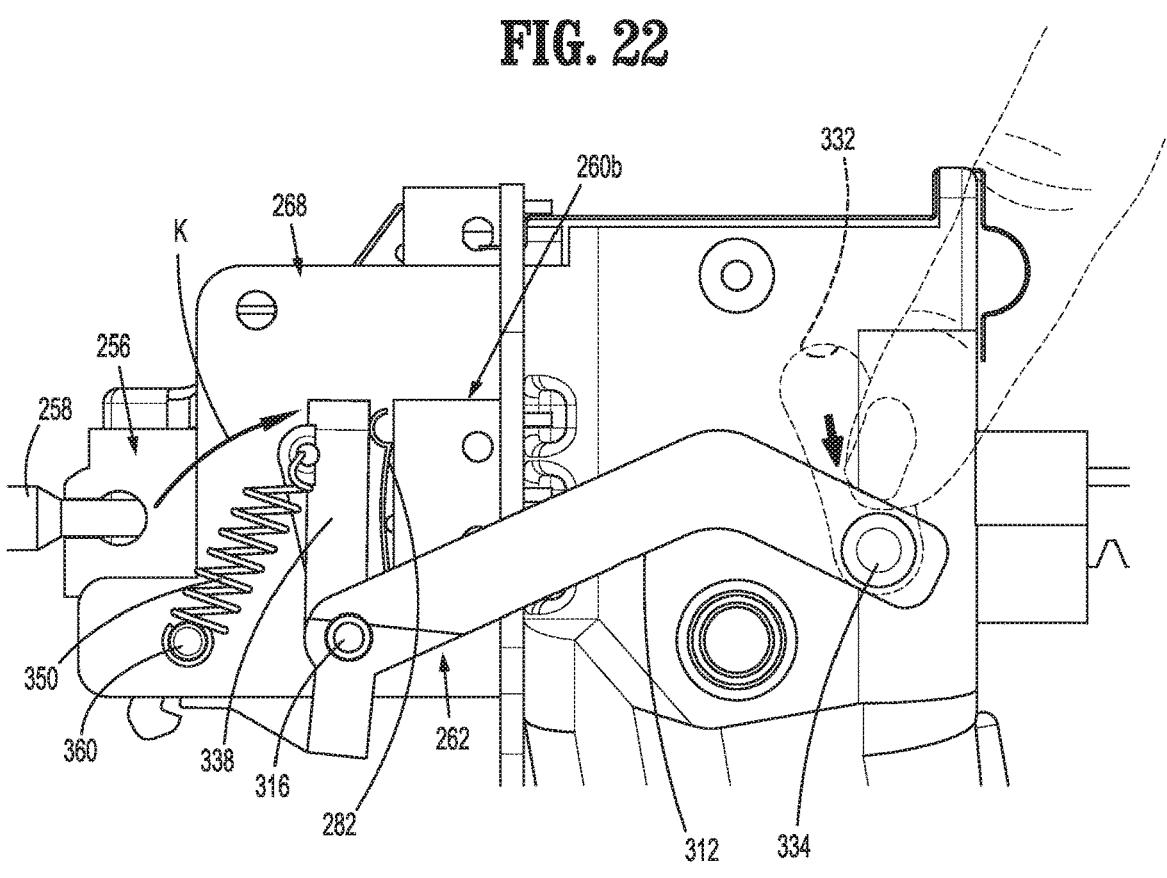
FIG. 23 is a side view of the internal components of the handle assembly shown in FIG. 15 in a clamped, pre-fired position of the stapling device with the safety trigger assembly in a fire-ready position.

FIGS. 21 and 22 illustrate internal components of the handle assembly 212 of the stapling device 10 (FIG. 1) in the clamped, pre-fired position with the safety trigger assembly 262 in the intermediate position. When the stapling device 10 is actuated by depressing the actuation button 20 (FIG. 1) on the handle assembly 212 to move the tool assembly 16 (FIG. 1) from the unclamped position to the clamped position, the rack 256 moves in the direction of arrow "H" in FIG. 21 such that the angled shoulder 298 of the rack 256 engages the cam surface of the bias arm 270 to pivot the bias arm 270 in the direction of arrow "I" in FIG. 21. As the bias arm 270 rotates in the direction of arrow "I", the abutment member 292 of the bias arm 270 moves away from the hinge lever 282 of the first safety switch 260a to allow the first safety switch 260a to change to a first state. In this state of the first safety switch 260a, power to the motor/gear assembly 30 (FIG. 2) is disrupted to stop advancement of the rack 256 with the rack 256 in a rack clamped position.

As the bias arm 270 of the bias arm assembly 262 rotates in the direction of arrow "I" (FIG. 21), the abutment member 292 of the bias arm 270 engages the engagement surface 326 of the arm 320 of the first trigger member 310 to move the arm 320 in the direction of arrow "J" in FIG. 21 to pivot the safety trigger assembly 262 from the safe position to the intermediate position. When this happens, the safety buttons 322 and 334 move to a central portion of the curved slots 332 of the outer housing 218 at a position spaced from the safety button shields 390 (FIG. 18) to a position that is accessible to a clinician.

FIGS. 23 and 24 illustrate the internal components of the handle assembly 212 of the stapling device 10 (FIG. 1) in the clamped, pre-fired position with the safety trigger assembly 262 in the fire-ready position. To move the safety trigger assembly 262 from the intermediate position to the fire-ready position, a clinician engages one or both the safety buttons 322 and 334 (only safety button 334 is shown) and slides the safety buttons 322 and 334 downwardly in the direction of arrow within the curved slots 332 (FIG. 23) of the outer housing 218. When the safety buttons 322 and 334 are slid downwardly within the curved slots 332, the safety trigger assembly 262 rotates within the outer housing 218 of the handle assembly 212 in the direction of arrow "K" in FIG. 23 such that the biasing member mount 338 of the second trigger member 312 moves into engagement with the hinge lever 282 of the safety switch 260b to move the safety switch 260b to the second state. In this state, the actuation button 20 (FIG. 1) can be depressed to fire the stapling device 10. In addition, the cam surface 372 of the latch 266 separates and moves out of engagement with the bottom surface of the rack 256 such that the biasing member 374 pivots the latch 266 in the direction of arrow "L" in FIG. 24 to the latched position. When the safety trigger assembly 262 is moved to the fire-ready position and the latch 266 is in the latched position, the distally extending finger 354 of the retainer member 314 of the safety trigger assembly 262 is received within the pocket 370 of the latch 266 to retain the safety trigger assembly 262 in the fire-ready position.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure.

Accordingly, the disclosure is not to be limited by what has been particularly shown and described, except as indicated by the appended claims.

What is claimed is:

1. A powered handle assembly for a surgical device comprising:
   an outer housing defining a cavity;
   an actuation button supported on the outer housing;
   a rack supported within the outer housing, the rack having teeth and movable from a rack retracted position, to a rack clamp position, and subsequently to a rack advanced position;
   a motor/gear assembly associated with the rack, the motor/gear assembly operable to move the rack from the rack retracted position, to the rack clamp position, and subsequently to the rack advanced position;
   a first safety switch supported on an inner housing, the first safety switch movable between a first state and a second state, wherein in the second state, the actuation button is operable to supply power to the motor/gear assembly and in the first state, power is disrupted to the motor/gear assembly;
   a bias arm supported adjacent the first safety switch, the bias arm including a cam member and an abutment member, the bias arm movable between a first position and a second position, wherein in the first position, the abutment member is engaged with the first safety switch to position the first safety switch in the second state, and in the second position, the first safety switch is positioned in the first state, wherein the rack is configured to engage the bias arm as the rack moves from the rack retracted position to the rack clamp position to move the bias arm from the first position to the second position; and
   a safety trigger assembly including at least one safety button that extends through a slot in the outer housing, the safety trigger assembly movable from a safe position, through an intermediate position, to a fire-ready position to position the first safety switch in the second state.

2. The powered handle assembly of claim 1, further including a first biasing member positioned to urge the bias arm towards the second position.

3. The powered handle assembly of claim 2, wherein the rack is configured to engage the safety trigger assembly as the rack moves from the rack retracted position to the rack clamped position to move the safety trigger assembly from the safe position to the intermediate position.

4. The powered handle assembly of claim 3, wherein the outer housing includes a safety button shield positioned adjacent one end of the slot, the safety button shield extending partially about the at least one safety button when the safety trigger assembly is in the safe position to limit access to the at least one safety button.

5. The powered handle assembly of claim 4, wherein the rack defines a cam surface, and the safety trigger assembly includes a cam member that moves along the cam surface of the rack as the rack moves from the rack retracted position to the rack clamp position to move the safety trigger assembly from the safe position to the intermediate position.

6. The powered handle assembly of claim 1, further including a biasing member positioned to urge the safety trigger assembly towards the safe position.

7. The powered handle assembly of claim 6, further including a latch positioned to engage the safety trigger assembly to retain the safety trigger assembly in the fire-ready position.

8. The powered handle assembly of claim 7, wherein the safety trigger assembly includes a retainer member configured to engage the latch when the safety trigger assembly is in the fire-ready position to retain the safety trigger assembly in the fire-ready position.

9. The powered handle assembly of claim 1, wherein the first safety switch is a micro-switch.

10. A powered handle assembly for a surgical device comprising:

an outer housing defining a cavity;

an actuation button supported on the outer housing;

a rack supported within the outer housing, the rack having teeth and movable from a rack retracted position, to a rack clamp position, and subsequently to a rack advanced position;

a motor/gear assembly associated with the rack, the motor/gear assembly operable to move the rack from the rack retracted position, through the rack clamp position, and subsequently to the rack advanced position;

at least one safety switch supported on an inner housing, the at least one safety switch movable between first and second states;

a bias arm supported adjacent to the at least one safety switch and including a cam member and an abutment member, the bias arm movable between a first position and a second position, wherein in the first position, the abutment member is engaged with the at least one safety switch to position the at least one safety switch in the second state and in the second position, the at least one safety switch is positioned in the first state, wherein the rack is configured to engage the bias arm as the rack moves from the rack retracted position to the rack clamp position to move the bias arm from the first position to the second position; and a safety trigger assembly including at least one safety button that extends through a slot in the outer housing, the safety trigger assembly positioned to engage the at least one safety switch and movable from a safe position, through an intermediate position, to a fire-ready position to position the at least one safety switch in the second state, wherein the bias arm is positioned to engage the safety trigger assembly as the bias arm moves from the first position to the second position to move the safety trigger assembly from the safe position to the intermediate position.

11. The powered handle assembly of claim 10, wherein the outer housing includes a safety button shield positioned adjacent one end of the slot, the safety button shield extending partially about the at least one safety button when the safety trigger assembly is in the safe position to limit access to the at least one safety button.

12. The powered handle assembly of claim 10, further including a first biasing member positioned to urge the safety trigger assembly towards the safe position.

13. The powered handle assembly of claim 12, further including a second biasing member positioned to urge the bias arm towards the second position.

14. The powered handle assembly of claim 10, wherein the at least one safety switch includes a first safety switch and a second safety switch, and the abutment member of the bias arm is engaged with the first safety switch.

15. The powered handle assembly of claim 14, wherein the safety trigger assembly is positioned to engage the second safety switch.

16. The powered handle assembly of claim 15, further including a latch positioned to engage the safety trigger assembly to retain the safety trigger assembly in the fire-ready position.

17. The powered handle assembly of claim 16, wherein the safety trigger assembly includes a retainer member configured to engage the latch when the safety trigger assembly is in the fire-ready position to retain the safety trigger assembly in the fire-ready position.

18. The powered handle assembly of claim 10, wherein the at least one safety switch is a micro-switch.

* * * * *